United States Patent
Reents et al.

(10) Patent No.: US 11,969,426 B2
(45) Date of Patent: Apr. 30, 2024

(54) PHARMACEUTICAL COMPOSITIONS COMPRISING AKT PROTEIN KINASE INHIBITORS

(71) Applicant: Genentech, Inc., South San Francisco, CA (US)

(72) Inventors: Reinhard Reents, Basel (CH); Pirmin Hidber, Basel (CH); Andre Hell, Basel (CH); Peter Steidle, Basel (CH); Martin Wunderlich, Basel (CH); Marie Pepelnjak, Basel (CH); Francis Gosselin, South San Francisco, CA (US); Edward Yost, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 17/724,045

(22) Filed: Apr. 19, 2022

(65) Prior Publication Data

US 2022/0241279 A1    Aug. 4, 2022

Related U.S. Application Data

(62) Division of application No. 15/672,505, filed on Aug. 9, 2017, now Pat. No. 11,337,977.

(60) Provisional application No. 62/373,252, filed on Aug. 10, 2016.

(51) Int. Cl.
*A61K 31/517* (2006.01)
*A61K 9/20* (2006.01)
*A61K 9/28* (2006.01)

(52) U.S. Cl.
CPC .......... *A61K 31/517* (2013.01); *A61K 9/2009* (2013.01); *A61K 9/2018* (2013.01); *A61K 9/2027* (2013.01); *A61K 9/2054* (2013.01); *A61K 9/2059* (2013.01); *A61K 9/2077* (2013.01); *A61K 9/2095* (2013.01); *A61K 9/28* (2013.01); *A61K 9/284* (2013.01)

(58) Field of Classification Search
CPC .. A61K 31/517; A61K 9/2009; A61K 9/2018; A61K 9/2027; A61K 9/2054; A61K 9/2059; A61K 9/2077; A61K 9/2095; A61K 9/28; A61K 9/284; A61K 9/2013; A61P 43/00; A61P 35/00
See application file for complete search history.

(56) References Cited

U.S. PATENT DOCUMENTS

| | | | |
|---|---|---|---|
| 8,063,050 | B2 | 11/2011 | Mitchell et al. |
| 8,853,199 | B2 | 10/2014 | Mitchell et al. |
| 9,315,471 | B2 | 4/2016 | Babu et al. |
| 9,416,110 | B2 | 8/2016 | Askin et al. |
| 9,676,730 | B2 | 6/2017 | Askin et al. |
| 9,790,190 | B2 | 10/2017 | Askin et al. |
| 9,905,725 | B2 | 2/2018 | Lee |
| 11,337,977 | B2 | 5/2022 | Reents et al. |
| 2004/0010000 | A1 | 1/2004 | Ayer et al. |
| 2007/0122482 | A1 | 5/2007 | Holm et al. |
| 2008/0051399 | A1 | 2/2008 | Mitchell et al. |
| 2009/0253720 | A1 | 10/2009 | Roberts et al. |
| 2011/0086102 | A1 | 4/2011 | Silver et al. |
| 2012/0183613 | A1 | 7/2012 | Demarini et al. |
| 2015/0306216 | A1 | 10/2015 | Baselga et al. |
| 2018/0055845 | A1 | 3/2018 | Reents et al. |

FOREIGN PATENT DOCUMENTS

| | | |
|---|---|---|
| WO | 2004006928 A1 | 1/2004 |
| WO | 2005041968 A2 | 5/2005 |
| WO | 2007118033 A1 | 10/2007 |
| WO | 2008006040 A1 | 1/2008 |
| WO | 2010084066 A1 | 7/2010 |
| WO | 2012088033 A2 | 6/2012 |
| WO | 2013173768 A1 | 11/2013 |
| WO | 2013173784 A1 | 11/2013 |
| WO | 2013173811 A1 | 11/2013 |
| WO | 2015073739 A1 | 5/2015 |
| WO | 2016012963 A1 | 1/2016 |
| WO | 2016063995 A1 | 4/2016 |

*Primary Examiner* — Robert A Wax
*Assistant Examiner* — Quanglong N Truong
(74) *Attorney, Agent, or Firm* — Mintz, Levin, Cohn, Ferris, Glovsky and Popeo, P.C.

(57) ABSTRACT

The present invention relates to pharmaceutical compositions comprising Akt protein kinase inhibitors with therapeutic activity against diseases such as cancer as well as processes for their preparation and their use as medicament.

20 Claims, 10 Drawing Sheets

PHARMACEUTICAL COMPOSITIONS COMPRISING AKT PROTEIN KINASE INHIBITORS

CROSS-REFERENCE TO RELATED APPLICATIONS

This application is a divisional of U.S. application Ser. No. 15/672,505 filed Aug. 9, 2017, issued as U.S. Pat. No. 11,337,977, which claims benefit of priority to U.S. Application No. 62/373,252 filed Aug. 10, 2016, which is herein incorporated by reference in its entirety and for all purposes.

FIELD OF THE INVENTION

The present invention relates to pharmaceutical compositions comprising Akt protein kinase inhibitors with therapeutic activity against diseases such as cancer as well as processes for their preparation and their use as medicament.

BACKGROUND OF THE INVENTION

The Protein Kinase B (PKB), also known as Akt, is a serine/threonine kinase that is overexpressed in certain human tumors. International Patent Application WO 2008/006040 (A1) and U.S. Pat. No. 8,063,050 (B2) discuss a number of inhibitors of Akt, including the compound (S)-2-(4-chlorophenyl)-1-(4-((5R, 7R)-7-hydroxy-5-methyl-6,7-dihydro-5H-cyclopenta[d]pyrimidin-4-yl)piperazin-1-yl)-3-(isopropylamino)propan-1-one with recommended INN ipatasertib (WHO Drug Information Vol. 27, No. 3, 2013, Recommended INN: List 70), which is being investigated in clinical trials for the treatment of various cancers.

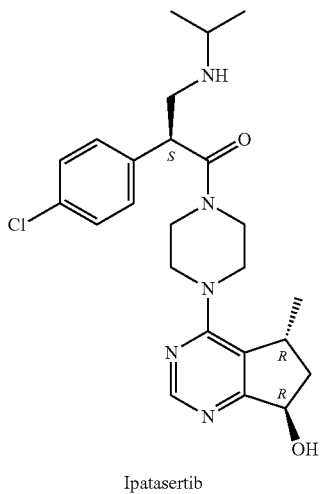

Ipatasertib

Stable, efficient and convenient pharmaceutical compositions are often required for active pharmaceutical ingredients. Provided herein are pharmaceutical compositions comprising an Akt inhibitior, particularly ipatasertib or pharmaceutically acceptable salts thereof, and one or more pharmaceutically acceptable excipients.

Only a few crystalline forms of ipatasertib have been described so far. For example, WO 2013/173784 A1 describes crystalline besylate and tosylate salts of ipatasertib. Both, benzene sulfonic acid and p-toluene sulfonic acid, are less-preferred anions for pharmaceutical salts.

The pharmaceutically best acceptable solid form of ipatasertib described to date is the amorphous anhydrous monohydrochloride salt which is described e.g. in WO 2013/173811 A1.

It has been found that ipatasertib monohydrochloride exhibits a unique mechanical behavior that involves highly brittle deformation characteristics (3× more brittle than lactose) making processing by mechanical compression very difficult. Mechanical compression during tableting of conventional pharmaceutical compositions comprising ipatasertib leads to exhausted compressibility, followed by elastic recovery of the tablet upon decompression. Therefore conventional pharmaceutical compositions comprising ipatasertib monohydrochloride are not suitable for direct compression due to lamination problems (crack formation during decompression) which are detectable as small cracks and fractures of the tablet core (e.g. using X-ray microtomography). Industrially required high-speed tableting processes may not be achievable.

It has been found that ipatasertib exhibits a very high solubility (>1 g/g water; >2 g/g water/ethanol 1:1) and a very high hygroscopicity (~6% at 50% RH, >35% at 95% RH). Whereas poor solubility is often a limiting factor in the development of galenical formulations of other API's (active pharmaceutical ingredient), a high solubility can equally be problematic for the process performance. Due to this very high intrinsic hygroscopicity of the API, ipatasertib drug substance tends to auto-dissolve to a honey-like viscous liquid at increased humidity. Such high solubility and hygroscopicity may pose serious problems for processing as well as for stability and shelf-life of the final product. Therefore, conventional pharmaceutical compositions comprising ipatasertib and processes for the manufacture of pharmaceutical compositions comprising wetting (e.g. wet granulation) are difficult due to the high solubility and high hygroscopicity of the API.

It has been further found that alternative granulation processes for ipatasertib such as high-shear processes with sequential wetting and drying are very difficult to control, do not lead to constant high-quality product and require high amounts of moisture adsorbent (at least 10-15% wt).

Due to the high solubility and hygroscopicity of ipatasertib, conventional processes for the manufacture of amorphous ipatasertib monohydrochloride often require long drying times at high temperatures and mandatory removal of pharmaceutically less-preferred solvents which can provoke partial crystallization. Conventional methods for the manufacture of amorphous ipatasertib monohydrochloride are not suitable to provide uniform, amorphous and stable API which exhibits particle properties suitable to be employed in the formulation process without further conditioning or reworking. There is thus a need for improved processes for the manufacture of amorphous ipatasertib monohydrochloride which can readily employed in the manufacture of pharmaceutical compositions.

BRIEF SUMMARY OF THE INVENTION

Provided herein are pharmaceutical compositions comprising ipatasertib and processes for manufacturing them, wherein the above mentioned problems have been solved.

The inventors of present application found that pharmaceutical compositions comprising ipatasertib and a certain amount of an intragranular material with plastic deformation characteristics prevent the formation of brittle cracks during compression. Tablet cores comprising ipatasertib and a pharmaceutically acceptable excipient with plastic deformation characteristics thus substantially improve processability.

The inventors of present application found that pharmaceutical compositions comprising ipatasertib and a certain amount of intragranular moisture adsorbent can prevent processing issues upon the dissolution of ipatasertib during granulation. Pharmaceutical compositions comprising ipatasertib and a certain amount of intragranular moisture adsorbent thus substantially improve processability.

The inventors of present application surprisingly found that fluid bed granulation is a well controllable process suitable to provide granules comprising ipatasertib in high and constant quality.

As described above, the only solid form of ipatasertib suitable for pharmaceutical development and manufacture known to date is the amorphous anhydrous monohydrochloride salt (ipatasertib•HCl).

Conventional drying processes of ipatasertib have been found to yield only moderate results due to the high solubility and hygroscopicity of the API as well as the complex de-solvatisation. Long drying times at high temperatures and mandatory removal of pharmaceutically less preferred or even non-acceptable solvents are required to comply with the standards of the International Council on Harmonisation of Technical Requirements for Registration of Pharmaceuticals for Human Use (ICH). In addition, conventional drying processes yield mixtures of amorphous material and partially crystalline material.

Ipatasertib monohydrochloride ethyl acetate monosolvate has a defined stoichiometry comprising one ethyl acetate molecule per ipatasertib molecule. Through conventional drying processes, the amount of ethyl acetate per ipatasertib in ipatasertib monohydrochloride ethyl acetate monosolvate can be reduced to a residual solvent content of 2 to 10% wt of ethyl acetate, typically 5 to 7% wt of ethyl acetate. Further reduction of ethyl acetate content, e.g. below 0.5% wt can be achieved only through harsh and lengthy drying conditions.

Ipatasertib monohydrochloride is obtained from ipatasertib monohydrochloride ethyl acetate. It has now been found that moisture is a key driving force in the conversion of ipatasertib•HCl•EtOAc to amorphous ipatasertib•HCl.

Drying/wetting cycles using vacuum drying and humidified nitrogen in a conical screw dryer, allow for removal of EtOAc and achievement of amorphous conversion. Drying time is however not significantly improved—still several days are often required for completion of a conventional batch on industrial scale. In addition, variations of solid state were observed in XRPD patterns. Further particle size distribution could not be controlled yielding only inconsistent particle size distribution profiles.

WO 2013/173811 A1 discloses the manufacture of amorphous ipatasertib monohydrochloride by spray drying (Examples 12 A-C, [00138]) using a two-fluid nozzle spray-dryer. It has been found that spray-drying processes as described in prior art yield only moderate results in regard of particle size and particle shape, i.e. bimodal particle size distribution with a high number of sub-micrometer particles is obtained. Flowability and processability of such obtained material is therefore very limited.

The present application further provides an improved spray drying process, devoid of problematic solvents, for the manufacture of amorphous ipatasertib•HCl from solid ipatasertib, particularly an ipatasertib solvate (e.g. ipatasertib•HCl•EtOAc), yielding chemically stable uniform amorphous material with improved flowability, bulk density, particle shape and particle size distribution which can be employed in the process for the manufacture of a pharmaceutical composition as disclosed herein without additional treatment, conditioning or reworking. The product obtained in the process described herein yields consistent and robust qualities across batches.

It has surprisingly been found that spray drying from water as solvent yields particularly beneficial results since ipatasertib has been found not to form hydrates nor other crystalline forms from water, since the high solubility of ipatasertib in water allows high API concentrations, and/or because water is considered to be safe contrary to many organic solvents.

It was found that spray-drying processes using a rotary wheel type atomizer as described in the examples can provide amorphous ipatasertib•HCl of up to >99.4% purity.

The spray-drying process described herein using a rotary wheel type atomizer as described in the examples provide the advantage that both residual EtOAc and water are instantaneously controlled—in some instances, no post-drying is needed to reach ICH Q3C(R5) limits.

The materials as obtained in the spray-drying process described herein using a rotary wheel type atomizer exhibit powder properties according to flow behaviour, PSD profiles and SEM images.

Due to the increased particle size of the material as obtained in exemplary spray-drying process described herein as compared to material obtained through conventional process, processability of the API is improved and disintegration of tablets comprising the material is improved.

The bulk density of the materials as obtained in the spray-drying process described herein using a rotary wheel type atomizer is increased nearly ~2-fold relative to materials as obtained in other conventional process. The bulk density has a very high impact e.g. also on subsequent tableting processes.

DETAILED DESCRIPTION OF THE INVENTION

Figure 1:
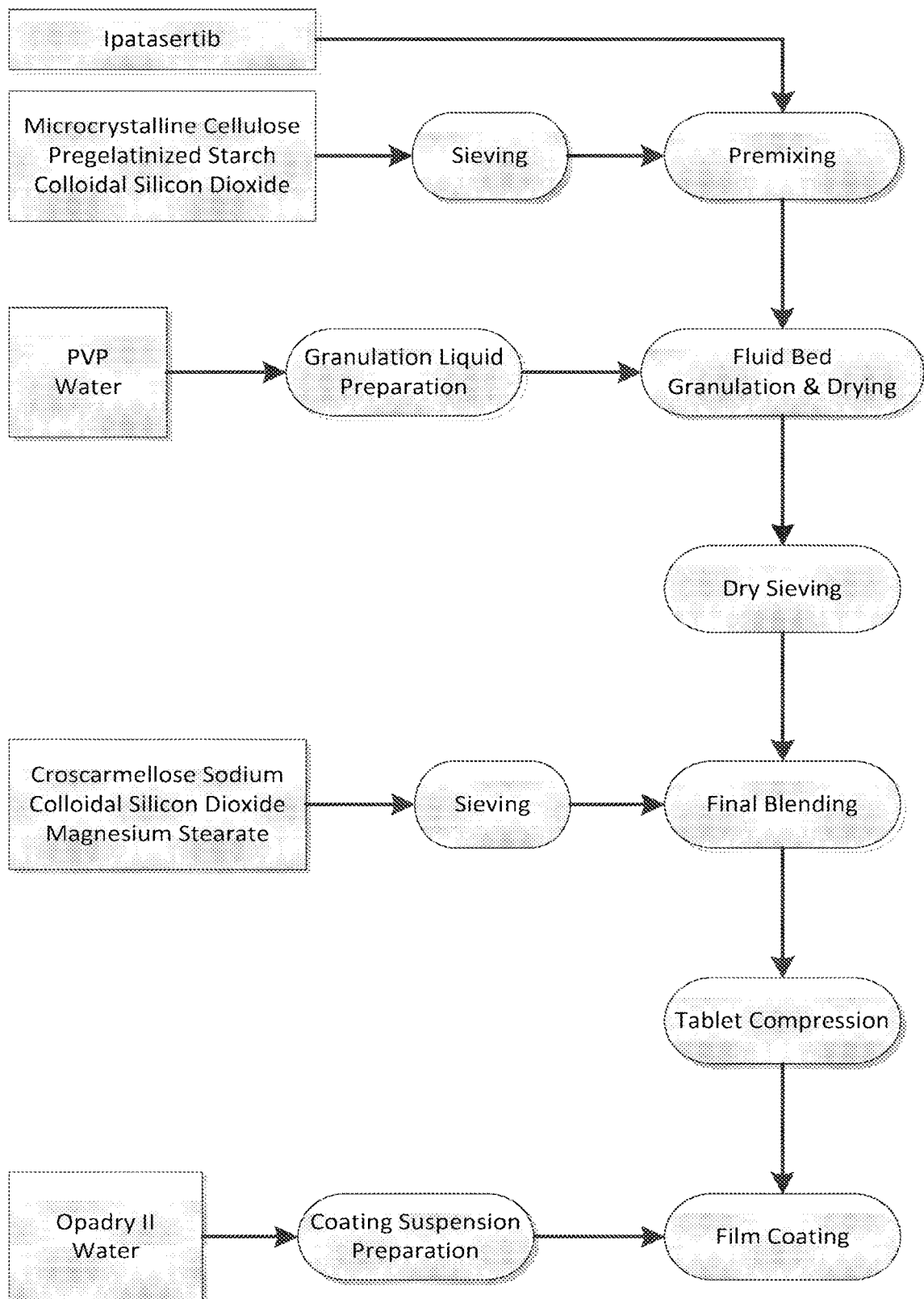
FIG. 1 illustrates a flow diagram of manufacturing process of the pharmaceutical compositions described herein.

The term "ipatasertib•HCl•EtOAc" as used herein refers to ipatasertib monohydrochloride comprising ethyl acetate in the crystal lattice, particularly comprising more than 0.5% wt ethyl acetate in the crystal lattice, more particularly comprising more than 2% wt ethyl acetate in the crystal lattice, most particularly comprising more than 5% wt ethyl acetate in the crystal lattice.

The term "tablet lamination" denotes the (partial) separation of a tablet into two or more distinct layers. Lamination may be caused by air-entrapment during compression and subsequent release on ejection or over-compression during tableting leading to distortion of granules in order that they no longer lock together. Lamination can also occur when groups of fine and light particles do not lock together.

The indication "% wt" indicates the mass percentage based on overall weight of tablet core (or if indicated based on overall weight of final film coated tablet).

A "fluidized bed" occurs when a quantity of solid particles are placed under appropriate conditions to cause the mixture to behave as a fluid. This is typically done by forcing pressurized air, gas, or other fluids through the bed of solid particles. This causes the solid medium to acquire properties and attributes similar to those of normal fluids, resulting in what is known as fluidization. Fluidized beds are commonly used in the pharmaceutical industry to dry, granulate, and coat any number of different active pharmaceutical ingredients (APIs), excipients, or other formulations.

The "fluid bed granulation" process involves suspending particles in an air stream (i.e. fluidizing particles) and spraying a liquid onto the fluidized bed, either from the top of the system down onto the fluidized bed (top-spray granulator) or from below upwards (bottom-spray granulator or Wurster process). Particles in the path of the spray get slightly wet and become sticky. The sticky particles collide with other particles in the bed of material and adhere to them to form granules. There are two different modes of fluid bed granulating: wet stage and dry stage.

In dry stage granulation, the particles only require a slight wetting to become tacky and stick to each other. The granulating solution is applied at a rate less than or equal to its evaporation rate. Thus, the particles remain "dry" through the entire process.

In wet stage granulation, the particles require a significant amount of moisture or granulating solution before they become tacky enough to stick to each other. The granulating solution is applied at a rate higher than the evaporation rate until the particles build up enough moisture to granulate. Note: The characteristics of the particles when wet and the type of granulating solution being used will determine which mode of granulating is most appropriate. While dry stage is more common, wet stage granulating allows for denser products. In one embodiment the fluid-bed granulator is a top-spray granulator in dry stage mode.

The terms "atomization" and "nebulization" both refer to the process of preparing an aerosol, i.e. a dispersion, particularly a colloidal dispersion, of solid particles or liquid droplets in a gas.

The term "aqueous mist" refers to an aerosol comprising small droplets of water (diameter smaller than 10 µm, particularly smaller than 5 µm, most particularly smaller than 1 µm) suspended in a gas, particularly in air or nitrogen, most particularly in nitrogen.

The term "atomizer" denotes a device that facilitates atomization of a dispersion of solid particles or liquid droplets into an aerosol. Atomizers and applications thereof are described for e.g. in Nasr, G. G. et al., Industrial Sprays and Atomization: Design, Analysis and Applications, Springer, 2002, ISBN 978-1852334604.

Atomizers can be categorized based on the energy input used to cause atomization, the breakup of the fluid into drops. Atomizers include:
single-fluid nozzles such as plain-orifice nozzles, shaped-orifice nozzles, surface-impingement single-fluid nozzles, pressure-swirl single-fluid spray nozzles, solid-cone single-fluid nozzles and compound nozzles;
two-fluid nozzles, such as internal-mix two-fluid nozzles and external-mix two-fluid nozzles;
rotary atomizers;
ultrasonic atomizers;
electrostatic atomizers.

Exemplary atomizers include two-fluid nozzles and rotary atomizers. In one embodiment the atomizer described herein is a rotary atomizer.

The term "rotary wheel type atomizer", also referred to as "rotary wheel atomizer" or "rotary atomizer" refers to a device used for atomization, wherein the feed is centrifugally accelerated to high velocity in the atomizer. The degree of atomization depends upon peripheral speed, feed rate, liquid properties and atomizer wheel design.

The term "rotary wheel type spray-dryer", also referred to as "rotary wheel spray-dryer" or "rotary spray-dryer" refers to a device comprising a rotary atomizer. A rotary spray-dryer is used for atomization and drying, wherein the feed is centrifugally accelerated to high velocity in the atomizer wheel before being discharged into the hot drying gas. The degree of atomization and particle morphology depends upon peripheral speed, feed rate, liquid properties and atomizer wheel design. Particle size is adjusted by changing the peripheral speed. Particular rotary wheel type spray-dryers comprise 24 holes.

The term "two-fluid nozzle" or "two-fluid nozzle atomizer" refers to a device used for atomization, wherein atomization is achieved pneumatically by high-velocity compressed gas (e.g. air or nitrogen, particularly nitrogen) impacting the liquid feed.

The term "two-fluid nozzle spray-dryer" refers to a device used for atomization and drying, wherein atomization is achieved pneumatically by high-velocity compressed gas (e.g. air or nitrogen, particularly nitrogen) impacting the liquid feed. Particle size is controlled by varying the nozzle flow ratio between atomizing gas and feed. Two-fluid nozzle spray-dryer can be operated in a) co-current mode or b) fountain (counter-current) mode.

a) When operating in co-current mode the flow directions of atomized material and the drying gas are identical, the nozzle tip is placed close to the outlet of the ceiling gas disperser. The co-current mode is selected when drying heat-sensitive products.

b) In fountain or counter-current mode, the flow directions of atomized material and the drying gas are counter-directional. Two-fluid nozzle in fountain mode is appropriate when coarse particles of a non-heat-sensitive feed are desired, the two-fluid nozzles can be further grouped into 1) internal-mix two-fluid nozzles and 2) external-mix two-fluid nozzles, depending on the mixing point of the gas and liquid streams relative to the nozzle face.

1) Internal-mix two-fluid nozzles contact fluids inside the nozzle. Shearing between high velocity gas and low velocity liquid disintegrates the liquid stream into droplets, producing a high velocity spray. This type of nozzle tends to use less atomizing gas than an external-mix atomizer and is better suited to higher viscosity streams.

2) External-mix two-fluid nozzles (or outside-mix two-fluid nozzles) contacts fluids outside the nozzle. This type of spray nozzle may need more atomizing air and a higher atomizing air pressure drop because the mixing and atomization of liquid takes place outside the nozzle. The liquid pressure drop is lower for this type of nozzle, sometimes drawing liquid into the nozzle due to the suction caused by the atomizing air nozzles (siphon nozzle).

The terms "single-fluid nozzle spray-dryer" or "pressure nozzle spray-dryer" refer to a device used for atomization and drying, wherein atomization is the result of the conversion of pressure energy within the liquid feed into kinetic energy of a moving thin liquid sheet. No compressed atomizing gas is present. Pressure applied to the liquid within the nozzle forces the liquid out of the orifice creating the atomization. A pressure nozzle can be operated in co-current mode or in fountain mode. Particle size is adjusted by changing the feed pressure and nozzle size. Pressure nozzles will generally deliver a narrower particle size distribution and coarser particles than other atomizer types. Selection of nozzle type depends on the feed properties and powder specification.

The term "cyclonic separation" refers to a filterless method of removing solid particulates from a gas or liquid stream through vortex separation, i.e. through rotational effects and gravity. A high speed rotating flow is established within a cylindrical or conical container called a cyclone. The stream flows in a helical pattern, beginning at the top (wide end) of the cyclone and ending at the bottom (narrow) end before exiting the cyclone. Denser particles in the rotating stream have too much inertia to follow the tight curve of the stream, and strike the outside wall, then fall to the bottom of the cyclone where they can be removed.

In a conical system, as the rotating flow moves towards the narrow end of the cyclone, the rotational radius of the stream is reduced, thus separating smaller and smaller particles. The cyclone geometry, together with flow rate, defines the cut point of the cyclone. This is the size of particle that will be removed from the stream with a 50% efficiency. Particles larger than the cut point will be removed with a greater efficiency and smaller particles with a lower efficiency.

The term "solid form" or "form" is a general term to denote a crystal form and/or amorphous form of a solid material.

The terms "crystal form" and "crystalline form" can be used interchangeably to denote polymorphs and pseudo-polymorphs of a crystalline solid.

The terms "polymorph" and "modification" can be used synonymously to denote one particular crystal structure in which a compound can crystallize. Different polymorphs have different arrangements or conformations of the molecules in the crystal lattice but all share the same elemental composition.

The term "polymorphism" denotes the ability of a compound to form more than one polymorph.

The terms "solvate" and "pseudo-polymorph" can be used synonymously to denote a crystal having either stoichiometric or nonstoichiometric amounts of a solvent incorporated in the crystal lattice. If the incorporated solvent is water, the solvate formed is a "hydrate". When the incorporated solvent is alcohol, the solvate formed is an "alcoholate".

The term "salt" denotes a material which is composed of two components, an acid and a base with a clearly defined stoichiometric ratio of the two salt formers. Salt crystals are formed by ionic bonding interactions with complete transfer of hydrogen ions between acid and base.

The term "agglomerate" denotes an assemblage of primary particles which are rigidly joined together as by fusion, sintering or growth. Agglomerates cannot be readily dispersed. The term "agglomeration" denotes a process by which primary particles are joined together to form an agglomerate.

The term "aggregate" denotes an assemblage of primary particles which are loosely attached to each other by contact. Aggregates can be readily dispersed. The term "aggregation" denotes a process by which primary particles are attached to each other to form an aggregate.

The term "amorphous form" denotes a solid material which does not possess a distinguishable crystal lattice and the molecular arrangement of molecules lacks a long-range order. In particular, amorphous denotes a material that does not show a sharp Bragg diffraction peak. Bragg's law describes the diffraction of crystalline material with the equation "2d·sin(theta)=n·lambda", wherein "d" denotes perpendicular distance (in Angstroms) between pairs of adjacent planes in a crystal ("d-spacing"), "theta" denotes the Bragg angle, "lambda" denotes the wavelength and "n" is an integer. When Bragg's law is fulfilled, the reflected beams are in phase and interfere constructively so that Bragg diffraction peaks are observed in the X-ray diffraction pattern. At angles of incidence other than the Bragg angle, reflected beams are out of phase and destructive interference or cancellation occurs. Amorphous material does not satisfy Bragg's law and no sharp Bragg diffraction peaks are observed in the X-ray diffraction pattern. The XRPD pattern of an amorphous material is further characterized by one or more amorphous halos.

The term "XRPD" denotes the analytical method of X-Ray Powder Diffraction. The repeatability of the angular values is in the range of 2Theta±0.2°, more particularly in the range of 2Theta±0.1°. The term "approximately" given in combination with an angular value denotes the variance which is in the range of 2Theta±0.2°, particularly in the range of 2Theta±0.1°. The relative XRPD peak intensity is dependent upon many factors such as structure factor, temperature factor, crystallinity, polarization factor, multiplicity, and Lorentz factor. Relative intensities may vary considerably from one measurement to another due to preferred orientation effects. According to USP 941 (US Pharmacopoeia, 37th Edition, General Chapter 941), relative intensities between two samples of the same material may vary considerably due to "preferred orientation" effects. Anisotropic materials adopting preferred orientation will lead to anisotropic distribution of properties such as modulus, strength, ductility, toughness, electrical conductivity, thermal expansion, etc., as described e.g. in Kocks U. F. et al. (Texture and Anisotropy: Preferred Orientations in Polycrystals and Their Effect on Materials Properties, Cambridge University Press, 2000). In XRPD but also Raman spectroscopy, preferred orientations cause a change in the intensity distribution. Preferred orientation effects are particularly pronounced with crystalline APIs of relatively large particle size.

The terms "$d_{50}$ value" (sometimes also referred to as "d(0.5)-value") and "mass-median diameter" (or MMD) can be used interchangeably and denote the average particle size by mass, i.e. the average equivalent diameter of a particle, which is defined as the diameter where 50% (w) of the particles of the ensemble have a larger equivalent spherical diameter, and the other 50% (w) have a smaller equivalent spherical diameter. In analogy, the term "$d_{10}$-value" denotes the particle diameter wherein 10% (w) of the particles of the ensemble have a smaller equivalent spherical diameter. In analogy, the term "$d_{90}$-value" denotes the particle diameter wherein 90% (w) of the particles of the ensemble have a smaller equivalent spherical diameter.

Mass-based Particle Size Distribution (PSD) through sieve analysis (also known as gradation test) is a widely used sizing method for the determination of particle size and particle size distribution. The mass of material that is retained on a specific sieve (typically 50 μm to 800 μm sieve size in steps of 20 μm to 200 μm) is weighted and presented as a percentage of the total sampled material, i.e. the cumulative percent of the weight of particles with sizes smaller than the corresponding sieve. Therefore, a mass-based PSD is generated.

The value "characteristic particle size" (d') obtained through sieve analysis corresponds to a fictional sieve size at which 63.2% wt of the total sieved material is passing through the screen.

The term yield "as/is" indicates that no corrections were made e.g. to consider the amount of solvent in the crystal, i.e. the yield based on amount of ipatasertib•HCl•EtOAc initially employed.

The term yield "corrected" indicates that the yield in relation to the initial solids on dry basis (anhydrous ipatasertib•HCl).

The term "anhydrous" as used herein denotes a solid form which is devoid of water or other solvate molecules in the crystal lattice.

The terms "screening" and "sieving" both refer to the process of reducing particles in size by mechanically induced attrition through a screen. This process commonly is referred to as milling or deagglomeration.

Active Pharmaceutical Ingredient (API)

(S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one (ipatasertib) has been found to be a safe, potent and efficacious inhibitor of Akt suitable for use in the treatment of hyperproliferative disorders such as cancer. Dosage strengths of 100 mg or 200 mg of ipatasertib free base have been found to achieve efficacy for different clinical indications.

In one embodiment, the Akt inhibitor is (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one (ipatasertib) or a pharmaceutically acceptable salt thereof.

In one embodiment, the Akt inhibitor is (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one (ipatasertib) or a pharmaceutically acceptable salt thereof in amorphous form.

In one embodiment, the Akt inhibitor is (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one (ipatasertib) as free base.

In one embodiment, the Akt inhibitor is (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one as monohydrochloride salt (ipatasertib•HCl).

In one embodiment, the Akt inhibitor is anhydrous (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one (ipatasertib).

In one embodiment, the Akt inhibitor is (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one as monohydrochloride salt (ipatasertib•HCl) in amorphous form.

In one embodiment, the Akt inhibitor is anhydrous (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one as monohydrochloride salt (ipatasertib•HCl) in amorphous form.

In one embodiment, the pharmaceutical composition comprises 50 mg to 1000 mg of Akt inhibitor. In one embodiment, the pharmaceutical composition comprises 100 mg to 800 mg of Akt inhibitor. In one embodiment, the pharmaceutical composition comprises 100 mg to 300 mg of Akt inhibitor. In one embodiment, the pharmaceutical composition comprises 100 mg, 200 mg or 300 mg of Akt inhibitor.

Filler (Intragranular)

As described above, amorphous ipatasertib monohydrochloride is a highly brittle API making processing using direct compression very difficult. It has been found that microcrystalline cellulose with high plastic deformation characteristics as filler favorably compensates the brittle properties of ipatasertib. It has been further found, that the combination of microcrystalline cellulose and pregelatinized starch as fillers together with ipatasertib provide a composition with improved granulation performance, which without being bound by any particular theory, may be due to the water absorbing properties of pregelatinized starch and/or also to an improved compression performance as compared to compositions of microcrystalline cellulose and API alone.

It has been further found, that alternative fillers, such as e.g. mannitol and lactose decrease tablet hardness.

It has been further found, that alternative combinations of fillers such as e.g. microcrystalline cellulose combined with lactose, increase the risk of tablet lamination.

In one embodiment, the pharmaceutical composition comprises one or more fillers selected from microcrystalline cellulose, pregelatinized starch, corn starch, lactose, mannitol, calcium phosphate, hydroxypropylcellulose, polyethylenglycol, sorbitol, maltodextrine and dextrose.

In one embodiment, the pharmaceutical composition comprises one or two fillers selected from microcrystalline cellulose and pregelatinized starch.

In one embodiment, the pharmaceutical composition comprises microcrystalline cellulose and pregelatinized starch as fillers.

In one embodiment, the pharmaceutical composition comprises 20-75% wt of filler(s). In another embodiment, the pharmaceutical composition comprises 30-70% wt of filler(s). In another embodiment, the pharmaceutical composition comprises 40-65% wt of filler(s). In another embodiment, the pharmaceutical composition comprises 50-60% wt of filler(s).

In one embodiment, the pharmaceutical composition comprises 20-75% wt of intragranular filler(s). In one embodiment, the pharmaceutical composition comprises 30-70% wt of intragranular filler(s). In one embodiment, the pharmaceutical composition comprises 40-65% wt of intragranular filler(s). In one embodiment, the pharmaceutical composition comprises 50-60% wt of intragranular filler(s).

In one embodiment, the pharmaceutical composition comprises 20-65% wt microcrystalline cellulose as filler. In one embodiment, the pharmaceutical composition comprises 30-55% wt microcrystalline cellulose as filler. In one embodiment, the pharmaceutical composition comprises 40-50% wt microcrystalline cellulose as filler. In one embodiment, the pharmaceutical composition comprises 40-45% wt microcrystalline cellulose as filler.

In one embodiment, the pharmaceutical composition comprises 0-50% wt pregelatinized starch as filler. In one embodiment, the pharmaceutical composition comprises 0-30% wt pregelatinized starch as filler. In one embodiment, the pharmaceutical composition comprises 5-15% wt pregelatinized starch as filler. In one embodiment, the pharmaceutical composition comprises 10-15% wt pregelatinized starch as filler.

In one embodiment, the pharmaceutical composition comprises 20-65% wt microcrystalline cellulose and 0-50% wt pregelatinized starch as fillers. In one embodiment, the pharmaceutical composition comprises 30-55% wt microcrystalline cellulose and 0-30% wt pregelatinized starch as fillers. In one embodiment, the pharmaceutical composition comprises 40-50% wt microcrystalline cellulose and 5-15% wt pregelatinized starch as fillers. In one embodiment, the pharmaceutical composition comprises 40-45% wt microcrystalline cellulose and 10-15% wt pregelatinized starch as fillers.

Binder (Intragranular)

It surprisingly has been found, that particle properties of granules can be substantially improved by adding one or more binders to the intragranular matrix. For example, Povidone K90 (polyvinylpyrrolidone K 90 with average Mw 360,000) improves binding capacity, increases particle size distribution (PSD) of granules and improves particle shape (decrease of amount of fines) while not affecting dissolution performance and hardness. It has been found, that granules comprising Povidone K90 exhibit improved properties such as improved binding capacity (significantly better bonding of API), decreased friability of granules, increased granule PSD and decreased amount of fines as compared to Povidone K30 while maintaining similar dissolution and disintegration performance at comparable hardness.

In one embodiment, the pharmaceutical composition comprises one or more binders selected from polyvinylpyrrolidone, hydroxypropymethylcellulose, hydroxypropylcellulose, hydroxyethyl cellulose, methylcellulose, polyvinyl acetate, polyvinylacohol, gelatin and gum arabic.

In one embodiment, the pharmaceutical composition comprises one or more binders selected from Povidone K90, Povidone K30, hydroxypropymethylcellulose, hydroxypropylcellulose, hydroxyethyl cellulose, methylcellulose, polyvinyl acetate, polyvinylacohol, gelatin and gum arabic.

In one embodiment, the binder is polyvinylpyrrolidone.

In one embodiment, the binder is Povidone K90.

In one embodiment, the pharmaceutical composition comprises 0-10% wt of binder. In one embodiment, the pharmaceutical composition comprises 0-5% wt of binder In one embodiment, the pharmaceutical composition comprises 1.5-3.5% wt of binder.

In one embodiment, the pharmaceutical composition comprises 0-10% wt of intragranular binder. In one embodiment, the pharmaceutical composition comprises 0-5% wt of intragranular binder. In one embodiment, the pharmaceutical composition comprises 1.5-3.5% wt of intragranular binder.

In one embodiment, the pharmaceutical composition comprises 0-10% wt of Povidone K90 as binder, more particularly 0-5% wt, even more particularly 1.5-3.5% wt.

In one embodiment, the pharmaceutical composition comprises 0-10% wt of intragranular Povidone K90 as binder. In one embodiment, the pharmaceutical composition comprises 0-5% wt of intragranular Povidone K90 as binder. In one embodiment, the pharmaceutical composition comprises 1.5-3.5% wt of intragranular Povidone K90 as binder.

Disintegrant (Intragranular and/or Extragranular)

It has been surprisingly found, that disintegration characteristics and drug release profile can be improved by the additional use of a disintegrant. It has been found that croscarmellose sodium is a particularly beneficial (super) disintegrant which does not introduce peroxide into the pharmaceutical composition.

In one embodiment, the pharmaceutical composition comprises one or more disintegrants selected from croscarmellose sodium (internally cross-linked sodium carboxymethylcellulose, E468), crospovidone (polyvinylpolypyrrolidone, PVPP, E1202, a highly cross-linked modification of polyvinylpyrrolidone (PVP)), sodium starch glycolate, sodium alginate, starch, pectine, cellulose derivates, and calcium croscarmellose.

In one embodiment, the pharmaceutical composition comprises croscarmellose sodium as disintegrant.

In one embodiment, the pharmaceutical composition comprises 3-10% wt of disintegrant. In one embodiment, the pharmaceutical composition comprises 4-8% wt of disintegrant. In one embodiment, the pharmaceutical composition comprises 5-7% wt of disintegrant.

In one embodiment, the pharmaceutical composition comprises 3-10% wt of intragranular disintegrant. In one embodiment, the pharmaceutical composition comprises 4-8% wt of intragranular disintegrant. In one embodiment, the pharmaceutical composition comprises 5-7% wt of intragranular disintegrant.

In one embodiment, the pharmaceutical composition comprises 3-10% wt of extragranular disintegrant. In one embodiment, the pharmaceutical composition comprises 4-8% wt of extragranular disintegrant. In one embodiment, the pharmaceutical composition comprises 5-7% wt of extragranular disintegrant.

In one embodiment, the pharmaceutical composition comprises 3-10% wt of croscarmellose sodium as disintegrant. In one embodiment, the pharmaceutical composition comprises 4-8% wt of croscarmellose sodium as disintegrant. In one embodiment, the pharmaceutical composition comprises 5-7% wt of croscarmellose sodium as disintegrant.

In one embodiment, the pharmaceutical composition comprises 3-10% wt of intragranular croscarmellose sodium as disintegrant. In one embodiment, the pharmaceutical composition comprises 4-8% wt of intragranular croscarmellose sodium as disintegrant. In one embodiment, the pharmaceutical composition comprises 5-7% wt of intragranular croscarmellose sodium as disintegrant.

In one embodiment, the pharmaceutical composition comprises 3-10% wt of extragranular croscarmellose sodium as disintegrant. In one embodiment, the pharmaceutical composition comprises 4-8% wt of extragranular croscarmellose sodium as disintegrant. In one embodiment, the pharmaceutical composition comprises 5-7% wt of extragranular croscarmellose sodium as disintegrant.

In one embodiment, the disintegrant is extragranular.

Lubricant (Extragranular)

It has been found that efficient lubrication to support robust tablet compression can be achieved by the additional use of a lubricant. It has been found that stearic acid or magnesium stearate is a particularly beneficial lubricant suitable to achieve acceptable lubrication effects during tablet compression and while providing target drug release profile.

In one embodiment, the pharmaceutical composition further comprises one or more lubricants.

In one embodiment, the pharmaceutical composition further comprises one or more lubricants selected from magnesium stearate, sodium stearylfumarate, stearic acid, talc, calcium stearate, and stearylalcohol.

In one embodiment, the pharmaceutical composition further comprises magnesium stearate as lubricant.

In one embodiment, the pharmaceutical composition further comprises stearic acid as lubricant.

In one embodiment, the pharmaceutical composition comprises 0-5% wt of glidant. In one embodiment, the pharmaceutical composition comprises 0-3% wt of glidant. In one embodiment, the pharmaceutical composition comprises 0.5-1.5% wt of glidant.

In one embodiment, the pharmaceutical composition comprises 0-5% wt of extragranular glidant. In one embodiment, the pharmaceutical composition comprises 0-3% wt of extragranular glidant. In one embodiment, the pharmaceutical composition comprises 0.5-1.5% wt of extragranular glidant.

In one embodiment, the pharmaceutical composition comprises 0-5% wt of magnesium stearate as glidant. In one embodiment, the pharmaceutical composition comprises 0-3% wt of magnesium stearate as glidant. In one embodiment, the pharmaceutical composition comprises 0.5-1.5% wt of magnesium stearate as glidant.

In one embodiment, the pharmaceutical composition comprises 0-5% wt of extragranular magnesium stearate as glidant. In one embodiment, the pharmaceutical composition comprises 0-3% wt of extragranular magnesium stearate as glidant. In one embodiment, the pharmaceutical composition comprises 0.5-1.5% wt of extragranular magnesium stearate as glidant.

In one embodiment, the pharmaceutical composition comprises 0-5% wt of extragranular stearic acid as glidant. In one embodiment, the pharmaceutical composition comprises 0-3% wt of extragranular stearic acid as glidant. In one embodiment, the pharmaceutical composition comprises 0.5-1.5% wt of extragranular stearic acid as glidant.

Moisture Adsorbent (Intragranular)

As described above, amorphous ipatasertib monohydrochloride exhibits a very high solubility and a very high hygroscopicity which poses a challenge for processing as well as for stability and shelf-life of the final product.

It has been surprisingly found herein that pharmaceutical compositions comprising amorphous ipatasertib monohydrochloride and a moisture adsorbent (intragranular) can prevent the dissolution of amorphous ipatasertib monohydrochloride during granulation. Pharmaceutical compositions comprising amorphous ipatasertib monohydrochloride and a moisture adsorbent thus substantially improve processability by reducing the risk of overwetting and overgranulation and by improving process robustness.

In one embodiment, the pharmaceutical composition comprises one or more moisture adsorbents.

In one embodiment, the pharmaceutical composition comprises one or more moisture adsorbents selected from colloidal silica, fumed silica, non-fumed silica (Syloid®), pregelatinized starch, corn starch and croscarmellose.

In one embodiment, the moisture adsorbent is colloidal silica.

In one embodiment, the moisture adsorbent is colloidal fumed silica.

In one embodiment, the pharmaceutical composition comprises 0-10% wt of moisture adsorbent. In one embodiment, the pharmaceutical composition comprises 0-5% wt of moisture adsorbent. In one embodiment, the pharmaceutical composition comprises 2-4% wt of moisture adsorbent.

In one embodiment, the pharmaceutical composition comprises 0-10% wt of intragranular moisture adsorbent. In one embodiment, the pharmaceutical composition comprises 0-5% wt of intragranular moisture adsorbent. In one embodiment, the pharmaceutical composition comprises 2-4% wt of intragranular moisture adsorbent.

In one embodiment, the pharmaceutical composition comprises 0-10% wt of colloidal silica as moisture adsorbent. In one embodiment, the pharmaceutical composition comprises 0-5% wt of colloidal silica as moisture adsorbent. In one embodiment, the pharmaceutical composition comprises 2-4% wt of colloidal silica as moisture adsorbent.

In one embodiment, the pharmaceutical composition comprises 0-10% wt of intragranular colloidal silica as moisture adsorbent. In one embodiment, the pharmaceutical composition comprises 0-5% wt of intragranular colloidal silica as moisture adsorbent. In one embodiment, the pharmaceutical composition comprises 2-4% wt of intragranular colloidal silica as moisture adsorbent.

Glidant (Extragranular)

Glidant properties (e.g. blend flowability) can be improved and tablet lamination be reduced by the additional use of an extragranular glidant. It has been found that colloidal silica is a beneficial glidant to achieve suitable final blend flowability and to mitigate risk of lamination. A glidant was found to improve granulate flow to support robust tablet compression process and target content uniformity.

It has been found that magnesium stearate is a beneficial glidant to achieve suitable lubrication effect during tablet compression and drug release profile. The use of colloidal silica in the presence of magnesium stearate is particularly efficient in reducing the risk of tablet lamination.

In one embodiment, the pharmaceutical composition comprises one or more glidants.

In one embodiment, the pharmaceutical composition comprises one or more glidants selected from colloidal silica, talc, magnesium stearate, polyethylenglycol, calcium stearate and cethylalcohol.

In one embodiment, the pharmaceutical composition comprises colloidal silica as glidant.

In one embodiment, the pharmaceutical composition comprises 0-5% wt of glidant. In one embodiment, the pharmaceutical composition comprises 0-3% wt of glidant. In one embodiment, the pharmaceutical composition comprises 0.5-1.5% wt of glidant.

In one embodiment, the pharmaceutical composition comprises 0-5% wt of extragranular glidant. In one embodiment, the pharmaceutical composition comprises 0-3% wt of extragranular glidant. In one embodiment, the pharmaceutical composition comprises 0.5-1.5% wt of extragranular glidant.

In one embodiment, the pharmaceutical composition comprises 0-5% wt of colloidal silica as glidant. In one embodiment, the pharmaceutical composition comprises 0-3% wt of colloidal silica as glidant. In one embodiment, the pharmaceutical composition comprises 0.5-1.5% wt of colloidal silica as glidant.

In one embodiment, the pharmaceutical composition comprises 0-5% wt of extragranular colloidal silica as glidant. In one embodiment, the pharmaceutical composition comprises 0-3% wt of extragranular colloidal silica as glidant. In one embodiment, the pharmaceutical composition comprises 0.5-1.5% wt of extragranular colloidal silica as glidant.

In one embodiment, the pharmaceutically acceptable intragranular excipients comprise one or more filler, moisture adsorbent and binder.

In one embodiment, the pharmaceutically acceptable extragranular excipients comprise one or more disintegrant, lubricant and glidant.

In one embodiment, the pharmaceutically acceptable intragranular excipients comprise one or more filler, moisture adsorbent and binder and the pharmaceutically acceptable extragranular excipients comprise one or more disintegrant, lubricant and glidant.

In one embodiment, the pharmaceutically acceptable intragranular excipients comprise microcrystalline cellulose, pregelatinized starch, colloidal silicon dioxide, and povidone K90.

In one embodiment, the pharmaceutically acceptable extragranular excipients comprise croscarmellose sodium, colloidal silicon dioxide and magnesium stearate.

In one embodiment, the pharmaceutically acceptable intragranular: excipients comprise microcrystalline cellulose, pregelatinized starch, colloidal silicon dioxide, and povidone K90 and the pharmaceutically acceptable extragranular excipients comprise croscarmellose sodium, colloidal silicon dioxide and magnesium stearate.

Film Coating

Stability, appearance, swallowability and taste masking can be improved by the additional use of a non-functional film coating. It has been found that Opadry II®, particularly low titan dioxide Opadry II®, a PVA (polyvinyl alcohol) based film coating system, is a beneficial film coating suitable to achieve homogeneity of coat color and coat thickness.

In one embodiment, the pharmaceutical composition further comprises a film coating selected from a PVA based film coating or a HPMC based film coating.

In one embodiment, the pharmaceutical composition further comprises a film coating selected from Opadry® PVA based film coating or Opadry® HPMC based film coating.

In one embodiment, the pharmaceutical composition further comprises an Opadry II® PVA based film coating, particularly a low titanium dioxide grade Opadry II® PVA based film coating.

In one embodiment, the pharmaceutical composition comprises 0-7% wt of Opadry II® PVA based film coating. In one embodiment, the pharmaceutical composition comprises 1-6% wt of Opadry II® PVA based film coating. In one embodiment, the pharmaceutical composition comprises 3-5% wt of Opadry II® PVA based film coating.

Pharmaceutical Compositions

It has been found, that oral immediate-release film-coated tablets are particularly suitable dosage forms comprising amorphous ipatasertib monohydrochloride because of safety, efficacy and good patient compliance, e.g. easy to swallow as well as tasteless and odorless.

Pharmaceutical compositions described herein exhibit a good stability of more than 24 months without complex storage requirements.

In one embodiment herein is a pharmaceutical composition comprising an Akt inhibitor and one or more pharmaceutically acceptable excipients selected from fillers, binders and disintegrants as described herein.

In one embodiment herein is a pharmaceutical composition comprising (S)-2-(4-chlorophenyl)-1-(4-((5R, 7R)-7-hydroxy-5-methyl-6,7-dihydro-5H-cyclopenta[d]pyrimidin-4-yl)piperazin-1-yl)-3-(isopropylamino)propan-1-one (ipatasertib) or a pharmaceutically acceptable salt thereof and one or more pharmaceutically acceptable excipients selected from fillers, binders and disintegrants as described herein.

In one embodiment herein the pharmaceutical composition as described herein comprises (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one (ipatasertib) or a pharmaceutically acceptable salt thereof, one or more fillers, a binder and a disintegrant as described herein.

In one embodiment herein the pharmaceutical composition as described herein comprises an intragranular matrix which comprises (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one (ipatasertib) or a pharmaceutically acceptable salt thereof and one or more pharmaceutically acceptable excipients selected from fillers, binders and disintegrants as described herein.

In one embodiment is a pharmaceutical composition as described herein comprising 50 mg to 1000 mg of (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one (ipatasertib) or a pharmaceutically acceptable salt thereof.

In one embodiment is a pharmaceutical composition comprising an Akt inhibitor and one or more fillers as described herein.

In one embodiment is a pharmaceutical composition comprising an Akt inhibitor and a binder as described herein.

In one embodiment is a pharmaceutical composition comprising an Akt inhibitor, one or more fillers and a binder as described herein.

In one embodiment is a pharmaceutical composition comprising an Akt inhibitor, one or more fillers, a binder and a disintegrant as described herein.

In one embodiment is a pharmaceutical composition comprising an Akt inhibitor, one or more fillers, a binder, a disintegrant and a lubricant as described herein.

In one embodiment is a pharmaceutical composition wherein the intragranular matrix comprises an Akt inhibitor and one or more pharmaceutically acceptable excipients selected from fillers, binders and disintegrants as described herein.

In one embodiment is a pharmaceutical composition wherein the intragranular matrix comprises an Akt inhibitor and one or more fillers as described herein.

In one embodiment is a pharmaceutical composition wherein the intragranular matrix comprises an Akt inhibitor and a binder as described herein.

In one embodiment is a pharmaceutical composition wherein the intragranular matrix comprises an Akt inhibitor, one or more fillers and a binder as described herein.

In one embodiment is a pharmaceutical composition wherein the intragranular matrix comprises an Akt inhibitor, one or more fillers, a binder and a disintegrant as described herein.

In one embodiment is a pharmaceutical composition wherein the extragranular matrix comprises a disintegrant as described herein.

In one embodiment, the pharmaceutical composition further comprises a lubricant as described herein.

In one embodiment, the pharmaceutical composition further comprises an extragranular lubricant as described herein.

In one embodiment, the pharmaceutical composition further comprises a moisture adsorbent as described herein.

In one embodiment, the pharmaceutical composition further comprises an intragranular moisture adsorbent as described herein.

In one embodiment, the pharmaceutical composition further comprises a glidant as described herein.

In one embodiment, the pharmaceutical composition further comprises am extragranular glidant as described herein.

In one embodiment, the pharmaceutical composition further comprises a film coating as described herein.

In one embodiment, the pharmaceutical composition is suitable for oral administration.

In one embodiment, the pharmaceutical composition is solid.

In one embodiment, the pharmaceutical composition is a tablet, a capsule or a sachet, wherein the tablet, capsule or sachet comprises granules comprises an Akt inhibitor and one or more pharmaceutically acceptable excipients selected from fillers, binders and disintegrants as described herein.

In one embodiment, the pharmaceutical composition is a tablet, a capsule or a sachet, wherein the tablet, capsule or sachet comprises granules comprising an Akt inhibitor and one or more fillers as described herein.

In one embodiment, the pharmaceutical composition is a tablet, a capsule or a sachet, wherein the tablet, capsule or sachet comprises granules comprising an Akt inhibitor and a binder as described herein.

In one embodiment, the pharmaceutical composition is a tablet, a capsule or a sachet, wherein the tablet, capsule or sachet comprises granules comprising an Akt inhibitor, one or more fillers and a binder as described herein.

In one embodiment, the pharmaceutical composition is a tablet, a capsule or a sachet, wherein the tablet, capsule or sachet comprises granules comprising an Akt inhibitor, one or more fillers, a binder and a disintegrant as described herein.

In one embodiment, the pharmaceutical composition is a tablet.

In one embodiment, the pharmaceutical composition is an immediate-release film-coated tablet.

In one example, the pharmaceutical composition comprises:
- 20-40% wt ipatasertib or a pharmaceutically acceptable salt thereof,
- 20-65% wt microcrystalline cellulose as filler,
- 0-50% wt pregelatinized starch as filler,
- 0-10% wt colloidal silica as moisture adsorbent,
- 1-10% wt polyvinylpyrrolidone as binder,
- 0-5% wt colloidal silica as glidant,
- 3-10% wt croscarmellose sodium as disintegrant, and
- 0-5% wt magnesium stearate as lubricant.

In another example, the pharmaceutical composition comprises:
- 20-40% wt ipatasertib or a pharmaceutically acceptable salt thereof,
- 20-65% wt microcrystalline cellulose as filler,
- 0-50% wt pregelatinized starch as filler,
- 0-10% wt colloidal silica as moisture adsorbent,
- 1-10% wt polyvinylpyrrolidone as binder,
- 0-5% wt colloidal silica as glidant,
- 3-10% wt croscarmellose sodium as disintegrant,
- 0-5% wt magnesium stearate as lubricant,
wherein the net mass of ipatasertib free base is 50 mg to 800 mg.

In still another example, the pharmaceutical composition comprises:
- 20-40% wt of ipatasertib free base or ipatasertib mono hydrochloride salt,
- 40-45% wt microcrystalline cellulose as filler,
- 10-15% wt pregelatinized starch as filler,
- 2-4% wt colloidal silica as moisture adsorbent,
- 1.5-3.5% wt polyvinylpyrrolidone as binder,
- 0.5-1.5% wt colloidal silica as glidant,
- 5-7% wt croscarmellose sodium as disintegrant,
- 0.5-1.5% wt magnesium stearate as lubricant.

In yet another example, the pharmaceutical composition comprises:
- 20-40% wt of ipatasertib free base or ipatasertib mono hydrochloride salt,
- 40-45% wt microcrystalline cellulose as filler,
- 10-15% wt pregelatinized starch as filler,
- 2-4% wt colloidal silica as moisture adsorbent,
- 1.5-3.5% wt polyvinylpyrrolidone as binder,
- 0.5-1.5% wt colloidal silica as glidant,
- 5-7% wt croscarmellose sodium as disintegrant,
- 0.5-1.5% wt magnesium stearate as lubricant,
wherein the net mass of ipatasertib free base is 50 mg to 300 mg.

In another example, the pharmaceutical composition comprises:
- 95-105 mg of ipatasertib free base or the corresponding amount of ipatasertib mono hydrochloride salt,
- 150-155 mg microcrystalline cellulose as filler,
- 40-45 mg pregelatinized starch as filler,
- 8-12 mg colloidal silica as moisture adsorbent,
- 7-10 mg polyvinylpyrrolidone as binder,
- 2-5 mg colloidal silica as glidant,
- 20-22 mg croscarmellose sodium as disintegrant,
- 2-5 mg magnesium stearate as lubricant.

In one example, the pharmaceutical composition comprises:
- 99-101 mg of ipatasertib free base or the corresponding amount of ipatasertib mono hydrochloride salt,
- 151.5-153.5 mg microcrystalline cellulose as filler,
- 41-43 mg pregelatinized starch as filler,
- 9.5-11.5 mg colloidal silica as moisture adsorbent,
- 7.75-9.75 mg polyvinylpyrrolidone as binder,
- 2.5-4.5 mg colloidal silica as glidant,
- 20-22 mg croscarmellose sodium as disintegrant,
- 2.5-4.5 mg magnesium stearate as lubricant.

In another example, the pharmaceutical composition comprises:
- 195-205 mg of ipatasertib free base or the corresponding amount of ipatasertib mono hydrochloride salt,
- 300-310 mg microcrystalline cellulose as filler,
- 80-90 mg pregelatinized starch as filler,
- 19-23 mg colloidal silica as moisture adsorbent,
- 15-20 mg polyvinylpyrrolidone as binder,
- 5-10 mg colloidal silica as glidant,
- 40-44 mg croscarmellose sodium as disintegrant,
- 5-10 mg magnesium stearate as lubricant.

In another example, the pharmaceutical composition comprises:
- 199-201 mg of ipatasertib free base or the corresponding amount of ipatasertib mono hydrochloride salt, 304.5-306.5 mg microcrystalline cellulose as filler,
83-85 mg pregelatinized starch as filler,
20-22 mg colloidal silica as moisture adsorbent,
16.5-18.5 mg polyvinylpyrrolidone as binder,
6-8 mg colloidal silica as glidant,
41-43 mg croscarmellose sodium as disintegrant,
6-8 mg magnesium stearate as lubricant.

Manufacturing Process of Pharmaceutical Compositions

Further provided herein is a process for the manufacture of pharmaceutical compositions as described herein. In particular, provided is a process for the manufacture of pharmaceutical compositions according to FIG. 1.

In one embodiment is a process for the manufacture of granules suitable for further use in a pharmaceutical composition as described herein comprising the following steps:
 a) Optional sieving of the filler(s), optionally the disintegrant and (in case present) the moisture adsorbent by passing through a mill.
 b) Preparing a pre-blend by mixing the filler(s) and (in case present) the moisture adsorbent together with the API followed by introduction of this pre-blend into a fluid-bed granulator.
 c) Preparing a granulation solution by dissolving the binder in a solvent followed by stirring until a clear solution is obtained. Alternatively, the binder can be added already during pre-blend preparation in step b) in which case the granulation solution consists of solvent.
 d) Spraying of the granulation solution onto the fluidized pre-blend in the fluid-bed granulator to obtain wet granules.
 e) Optional drying of the obtained wet granules in the fluid-bed granulator.

In one embodiment is a process for the manufacture of a pharmaceutical composition as described herein comprising the following steps:
 a) Optional sieving of the filler(s) and (in case present) the moisture adsorbent by passing through a mill.
 b) Preparing a pre-blend by mixing the filler(s) and (in case present) the moisture adsorbent together with the API followed by introduction of this pre-blend into a fluid-bed granulator.
 c) Preparing a granulation solution by dissolving the binder in a solvent followed by stirring until a clear solution is obtained. Alternatively, the binder can be added already during pre-blend preparation in step b) in which case the granulation solution consists of solvent.
 d) Spraying of the granulation solution onto the fluidized pre-blend in the fluid-bed granulator to obtain wet granules.
 e) Optional drying of the obtained wet granules in the fluid-bed granulator.
 f) Optional sieving of the obtained granules by passing through a mill.
 g) Optional sieving of the disintegrant and (in case present) the glidant by passing through a mill.
 h) Preparing a first blend by mixing the disintegrant and (in case present) the glidant together with the dry granules in a blender. Alternatively or in addition, the disintegrant can be added already during pre-blend preparation in step b).
 i) Optional sieving of the lubricant by passing through a mill.
 j) Preparing a second blend by mixing the lubricant together with the first blend in a blender.
 k) Compression of the second blend to tablets using a tablet press and punches.
 l) Optional coating of the tablets in a pan coater.

In one embodiment, the mill in step a) has a sieve size of 1.0 mm to 2.0 mm. In another embodiment, the mill in step a) has a sieve size of 1.5 mm.

In one embodiment, the material sieved in step a) further comprises a binder as described herein.

In one embodiment, the material sieved in step a) further comprises a disintegrant as described herein.

In one embodiment, the material sieved in step a) further comprises a binder as described herein and a disintegrant as described herein.

In one embodiment, the pre-blend in step b) further comprises a binder as described herein.

In one embodiment, the pre-blend in step b) further comprises a disintegrant as described herein.

In one embodiment, the pre-blend in step b) further comprises a binder as described herein and a disintegrant as described herein.

In one embodiment, the fluid bed granulator in step b) is a top-spray granulator or a bottom-spray granulator.

In one embodiment, the fluid bed granulator in step b) is a top-spray granulator.

In one embodiment, the fluid bed granulator in step b) is a bottom-spray granulator.

In one embodiment, the pre-blend in b) is further mixed during a preheating phase at elevated temperatures, for example at 30 to 80° C. or 40 to 80° C.

In one embodiment, the pre-blend in b) is further mixed during a preheating phase at elevated temperatures, wherein the preheating phase lasts for less than 15 min, or less than 10 minutes, or less than 5 minutes.

In one embodiment, the granulation solution in step c) is prepared with a solvent comprising water.

In one embodiment, the granulation solution in step c) is prepared with water as solvent.

In one embodiment, the granulation solution in step c) is prepared at a temperature of 5 to 60° C. In one embodiment, the granulation solution in step c) is prepared at a temperature of at 20 to 30° C. In one embodiment, the granulation solution in step c) is prepared at a temperature of about 25° C. In one embodiment, the granulation solution in step c) is prepared at a temperature of 25° C.

In one embodiment, the spraying in step d) is performed at a spray pressure of the granulation solution of 0.1 to 5 bar. In one embodiment, the spraying in step d) is performed at a spray pressure of the granulation solution of 2 to 4 bar. In one embodiment, the spraying in step d) is performed at a spray pressure of the granulation solution of 1 to 3 bar.

In one embodiment, the spraying in step d) is performed at a spray rate of the granulation solution of 50 to 250 g/min. In one embodiment, the spraying in step d) is performed at a spray rate of the granulation solution of 50 to 200 g/min. In one embodiment, the spraying in step d) is performed at a spray rate of the granulation solution of 75 to 125 g/min.

In one embodiment, the spraying in step d) is performed using a spray nozzle of 0.8 to 2 mm, or 1.0 to 1.6 mm diameter, or 1.0 to 1.4 mm diameter. In one embodiment, the spraying in step d) is performed using a spray nozzle of 1.0 to 1.4 mm diameter.

In one embodiment, the drying in step e) is performed with air, particularly with air at a temperature of 50 to 80° C. In one embodiment, the drying in step e) is performed with air at a temperature of about 65° C.

In one embodiment, the drying in step e) is performed with air at an air flow of 300-600 m$^3$/h or 360-560 m$^3$/h.

In one embodiment, the drying in step e) takes place for less than about 1 h.

In one embodiment, the mill in step f) has a sieve size of 1.0 mm to 2.0 mm. In one embodiment, the mill in step f) has a sieve size of 1.5 mm.

In one embodiment, the mill in step g) has a sieve size of 1.0 mm to 2.0 mm. In one embodiment, the mill in step g) has a sieve size of 1.5 mm.

In one embodiment, the mill in step i) has a sieve size of 1.0 mm to 2.0 mm. In one embodiment, the mill in step i) has a sieve size of 1.5 mm.

In one embodiment, the compression in step k) takes place at a main compression force of 6 to 20 kN. In one embodiment, the compression in step k) takes place at a main compression force of 8 to 15 kN. In one embodiment, the compression in step k) takes place at a main compression force of 10 to 14 kN.

In one embodiment, the pharmaceutical composition comprises 95-105 mg of ipatasertib free base (or the corresponding amount of ipatasertib mono hydrochloride salt), and the compression in step k) takes place at a main compression force of 6 to 14 kN. In another embodiment, the pharmaceutical composition comprises 95-105 mg of ipatasertib free base (or the corresponding amount of ipatasertib mono hydrochloride salt), and the compression in step k) takes place at a main compression force of 8-10 kN.

In one embodiment, the pharmaceutical composition comprises 195-205 mg of ipatasertib free base (or the corresponding amount of ipatasertib mono hydrochloride salt), and the compression in step k) takes place at a main compression force of 9 to 20 kN. In another embodiment, the pharmaceutical composition comprises 195-205 mg of ipatasertib free base (or the corresponding amount of ipatasertib mono hydrochloride salt), and the compression in step k) takes place at a main compression force of 13 to 15 kN.

In one embodiment, the coating in step l) takes place in a pan coater wherein an aqueous coating suspension is sprayed on the tablet.

In one embodiment, the coating in step l) takes place in a pan coater wherein an aqueous coating suspension is sprayed on the tablet using a spray nozzle of 0.5 to 1.5 mm diameter. In one embodiment, the coating in step l) takes place in a pan coater wherein an aqueous coating suspension is sprayed on the tablet using a spray nozzle of 0.8 to 1.5 mm diameter. In one embodiment, the coating in step l) takes place in a pan coater wherein an aqueous coating suspension is sprayed on the tablet using a spray nozzle of 0.8 to 1.2 mm diameter.

In one embodiment, the coating in step l) takes place in a pan coater wherein an aqueous coating suspension is sprayed on the tablet at a spray pressure of 1.5 to 3 bar. In one embodiment, the coating in step l) takes place in a pan coater wherein an aqueous coating suspension is sprayed on the tablet at a spray pressure of 2 to 2.5 bar.

In one embodiment, the coating in step l) is followed by drying using air at an inlet temperature of 50 to 75° C., particularly 60° C., and at an inlet flow of 400 to 800 m³/h, particularly 450 m³/h.

Spray-Drying Process

Also provided herein is a spray-drying process, devoid of problematic solvents, for the manufacture of uniform and stable amorphous ipatasertib monohydrochloride particles with improved particle size, particle shape and particle properties, such as improved flowability and bulk density, which can be further employed in the manufacture of pharmaceutical compositions without additional treatment, conditioning or reworking.

Ipatasertib solvates have been successfully achieved with solvents selected from the following list:

| | |
|---|---|
| Methyl acetate | Methyl-tert-butyl ether |
| Ethyl acetate | Methyl-tert-butyl ether (water saturated |
| n-Propyl acetate | (ca. 1%) |
| Isopropyl acetate | Cyclopentyl methyl ether |
| n-Butyl acetate | 1,2-Dimethoxyethane |
| Isobutyl acetate | 1,2-Diethoxyethane |
| tert-butyl acetate | 2,2-Dimethoxypropane |
| Amyl acetate | 2-Methyltetrahydrofuran |
| Glycerol triacetate | |
| Ethyl propanoate | Tetrahydropyran |
| Methylethyl ketone | Chloroform |
| 2-Pentanone | Carbon tetrachloride |
| Methylbutyl ketone | 1,2-Dichloroethane |
| Methylisobutyl ketone | 1,1,1-Trichloroethane |
| Diisopropyl ketone | Trichloroethene |
| Diisobutyl ketone | Tetrachloroethylene |
| Dimethyl carbonate | Benzene |
| Diethyl carbonate | Toluene |
| Diethyl ether | Ethyl benzene |
| Chlorobenzene | |
| Cumene | |
| o-Xylene | |
| m-Xylene | |
| p-Xylene | |
| Tetralin. | |

Solvents can be based on a solvent which is classified as a USP Class 3 solvent (based on risk assessment or their potential toxicity level), which is water miscible, has a high vapor pressure and high volatility and should not form genotoxic side products.

Exemplary solvates of ipatasertib suitable as starting material in the manufacture of ipatasertib monohydrochloride (ipatasertib•HCl) are ipatasertib solvates comprising in the crystal lattice a solvent selected from the list consisting of methyl acetate, ethyl acetate, n-propyl acetate, isopropyl acetate, n-butyl acetate, isobutyl acetate, tert-butyl acetate, ethyl propanoate, methylethyl ketone, 2-pentanone, methylbutyl ketone, methylisobutyl ketone, diisopropyl ketone, diisobutyl ketone, and methyl-tert-butyl ether.

In one embodiment the solvates of ipatasertib suitable as starting material in the manufacture of ipatasertib monohydrochloride (ipatasertib•HCl) are ipatasertib solvates comprising in the crystal lattice a solvent selected from the list consisting of ethyl acetate, n-propyl acetate, n-butyl acetate, and methylethyl ketone.

In one embodiment, the solvate of ipatasertib suitable as starting material in the manufacture of ipatasertib monohydrochloride (ipatasertib•HCl) is ipatasertib ethyl acetate also known as ipatasertib ethyl ethanoate, which is characterized by a single crystal X-Ray diffraction pattern comprising peaks at an angle of diffraction 2Theta of 6.6°, 13.9°, 16.6°, 17.4°, 18.2°, 19.0°, 20.5°, 21.4°, 22.4° and 22.6° (±0.2°).

In one embodiment, the solvate of ipatasertib suitable as starting material in the manufacture of ipatasertib monohydrochloride (ipatasertib•HCl) is ipatasertib ethyl acetate also known as ipatasertib ethyl ethanoate, which is characterized by a single crystal X-Ray diffraction pattern comprising peaks at an angle of diffraction 2Theta of 6.6°, 13.9°, 16.6°, 17.4°, 18.2°, 19.0°, 20.5°, 21.4°, 22.4° and 22.6° (±0.1°).

In another embodiment, the solvate of ipatasertib suitable as starting material in the manufacture of ipatasertib monohydrochloride (ipatasertib•HCl) is ipatasertib ethyl acetate also known as ipatasertib ethyl ethanoate, which is characterized by an XRPD diffraction pattern comprising XRPD peaks at an angle of diffraction 2Theta of 6.6°, 8.4°, 10.5°, 13.6°, 16.4°, 17.2°, 18.8°, 20.0, 21.1° and 22.1° (±0.2°).

In another embodiment, the solvate of ipatasertib suitable as starting material in the manufacture of ipatasertib monohydrochloride (ipatasertib•HCl) is ipatasertib ethyl acetate also known as ipatasertib ethyl ethanoate, which is characterized by characterized by an XRPD diffraction pattern comprising XRPD peaks at an angle of diffraction 2Theta of 6.6°, 8.4°, 10.5°, 13.6°, 16.4°, 17.2°, 18.8°, 20.0, 21.1° and 22.1° (±0.1°).

A another embodiment, the solvate of ipatasertib suitable as starting material in the manufacture of ipatasertib monohydrochloride (ipatasertib•HCl) is ipatasertib n-propyl acetate also known as ipatasertib n-propyl ethanoate. One exemplary solid form of ipatasertib n-propyl acetate is characterized by an XRPD diffraction pattern comprising peaks at an angle of diffraction 2Theta of 6.2°, 6.9°, 9.5°, 14.4°, 16.9°, 17.4°, 18.0°, 19.8°, 20.7° and 22.1° (±0.2°).

A another embodiment, the solvate of ipatasertib suitable as starting material in the manufacture of ipatasertib monohydrochloride (ipatasertib•HCl) is ipatasertib n-propyl acetate also known as ipatasertib n-propyl ethanoate. One exemplary solid form of ipatasertib n-propyl acetate is characterized by an XRPD diffraction pattern comprising peaks at an angle of diffraction 2Theta of 6.2°, 6.9°, 9.5°, 14.4°, 16.9°, 17.4°, 18.0°, 19.8°, 20.7° and 22.1° (±0.1°).

Another exemplary solid form of ipatasertib n-propyl acetate is characterized by an XRPD diffraction pattern comprising peaks at an angle of diffraction 2Theta of 6.5°, 7.5°, 9.9°, 12.2°, 14.5°, 16.6°, 17.0°, 19.6°, 20.6° and 24.5° (±0.2°).

Another exemplary solid form of ipatasertib n-propyl acetate is characterized by an XRPD diffraction pattern comprising peaks at an angle of diffraction 2Theta of 6.5°, 7.5°, 9.9°, 12.2°, 14.5°, 16.6°, 17.0°, 19.6°, 20.6° and 24.5° (±0.2°).

Yet another exemplary solid form of ipatasertib n-propyl acetate is characterized by an XRPD diffraction pattern comprising peaks at an angle of diffraction 2Theta of 5.8°, 6.9°, 12.3°, 14.1°, 17.4°, 18.1°, 18.7°, 19.3°, 20.4° and 20.6° (±0.2°).

Yet another exemplary solid form of ipatasertib n-propyl acetate is characterized by an XRPD diffraction pattern comprising peaks at an angle of diffraction 2Theta of 5.8°, 6.9°, 12.3°, 14.1°, 17.4°, 18.1°, 18.7°, 19.3°, 20.4° and 20.6° (±0.1°).

Another exemplary solvate of ipatasertib suitable as starting material in the manufacture of ipatasertib monohydrochloride (ipatasertib•HCl) is ipatasertib n-butyl acetate also known as ipatasertib n-butyl ethanoate, which is characterized by an XRPD diffraction pattern comprising peaks at an angle of diffraction 2Theta of 5.8°, 7.5°, 12.0°, 13.7°, 14.8°, 16.9°, 18.8°, 19.1°, 21.8° and 22.7° (±0.2°).

In another embodiment, the solvate of ipatasertib suitable as starting material in the manufacture of ipatasertib monohydrochloride (ipatasertib•HCl) is ipatasertib n-butyl acetate also known as ipatasertib n-butyl ethanoate, which is characterized by an XRPD diffraction pattern comprising peaks at an angle of diffraction 2Theta of 5.8°, 7.5°, 12.0°, 13.7°, 14.8°, 16.9°, 18.8°, 19.1°, 21.8° and 22.7° (±0.1°).

Another exemplary solvate of ipatasertib suitable as starting material in the manufacture of ipatasertib monohydrochloride (ipatasertib•HCl) is ipatasertib methylethyl ketone also known as ipatasertib 2-butanone, which is characterized by an XRPD diffraction pattern comprising XRPD peaks at an angle of diffraction 2Theta of 5.8°, 7.6°, 12.0°, 13.8°, 14.7°, 16.3°, 17.1°, 18.8°, 19.1° and 22.8° (±0.2°).

In another embodiment, the solvate of ipatasertib suitable as starting material in the manufacture of ipatasertib monohydrochloride (ipatasertib•HCl) is ipatasertib methylethyl ketone also known as ipatasertib 2-butanone, which is characterized by characterized by an XRPD diffraction pattern comprising XRPD peaks at an angle of diffraction 2Theta of 5.8°, 7.6°, 12.0°, 13.8°, 14.7°, 16.3°, 17.1°, 18.8°, 19.1° and 22.8° (±0.1°).

In one embodiment, the solvate of ipatasertib suitable as starting material in the manufacture of ipatasertib monohydrochloride (ipatasertib•HCl) is ipatasertib ethyl acetate.

In another embodiment, the solvate of ipatasertib suitable as starting material in the manufacture of ipatasertib monohydrochloride (ipatasertib•HCl) is ipatasertib monohydrochloride ethyl acetate solvate (ipatasertib•HCl•EtOAc) comprising less than 10% wt of ethyl acetate.

In still another embodiment, the solvate of ipatasertib suitable as starting material in the manufacture of ipatasertib monohydrochloride (ipatasertib•HCl) is ipatasertib monohydrochloride ethyl acetate solvate (ipatasertib•HCl•EtOAc) comprising less than 8% wt of ethyl acetate.

In yet another embodiment, the solvate of ipatasertib suitable as starting material in the manufacture of ipatasertib monohydrochloride (ipatasertib•HCl) is ipatasertib monohydrochloride ethyl acetate solvate (ipatasertib•HCl•EtOAc) comprising less than 7% wt of ethyl acetate.

In another aspect provided herein is a process for the preparation of amorphous ipatasertib monohydrochloride comprising the steps of:
 a) Dissolution of a solvate of ipatasertib in a solvent;
 b) Feeding the obtained feed solution into a spray-dryer unit;
 c) Atomizing the solution in the drying chamber to yield a mist;
 d) Mixing the mist created with drying gas thereby evaporating the solvent;
 e) Separating the resulting amorphous ipatasertib monohydrochloride powder from the drying gas; and
 f) Collecting the obtained amorphous ipatasertib monohydrochloride powder.

In another aspect provided herein is a process for the preparation of amorphous ipatasertib monohydrochloride comprising the steps of:
 a) Dissolution of ipatasertib monohydrochloride ethyl acetate solvate (ipatasertib•HCl•EtOAc) in a solvent;
 b) Feeding the obtained feed solution into a spray-dryer unit;
 c) Atomizing the solution in the drying chamber to yield a mist;
 d) Mixing the mist created with drying gas thereby evaporating the solvent;
 e) Separating the resulting amorphous ipatasertib monohydrochloride powder from the drying gas; and
 f) Collecting the obtained amorphous ipatasertib monohydrochloride powder.

Optionally, the substantially powder-free drying gas comprising evaporated solvent may be recycled as follows:
 a) Directing the drying gas from the cyclone into a filter bag housing where very fine particles are retained in the bag filters.
 b) Cooling down the drying gas in a condenser to yield solvent condensation.
 c) Re-heating and re-circulation of the re-dried drying gas into the drying chamber.

In one embodiment, the process of the preparation of amorphous ipatasertib monohydrochloride (ipatasertib•HCl)

from ipatasertib monohydrochloride ethyl acetate solvate (ipatasertib•HCl•EtOAc) comprises using a spray dryer with a rotary wheel-type atomizer.

In one embodiment, the process of the preparation of amorphous ipatasertib monohydrochloride (ipatasertib•HCl) from an ipatasertib solvate comprises using a spray dryer with a rotary wheel-type atomizer.

In a particular embodiment, the dissolution of step a) takes place at a temperature of 5° C. to 50° C. The dissolution of step a) can take place at a temperature of 20° C. to 25° C.

In a particular embodiment, the solvent of step a) comprises water, wherein the water can be purified water.

In a particular embodiment, the feed solution obtained in step a) is an aqueous solution.

In one embodiment, the feed solution obtained in step a) comprises 5 to 35% (w/w) of ipatasertib•HCl•EtOAc. In another embodiment, the feed solution obtained in step a) comprises 10 to 30% (w/w) of ipatasertib•HCl•EtOAc. In still another embodiment, the feed solution obtained in step a) comprises 18-22% (w/w) of ipatasertib•HCl•EtOAc.

In one embodiment, the feed solution in step b) is fed at a feed rate of 7 to 20 kg/h. In one embodiment, the feed solution in step b) is fed at a feed rate of 10 to 12 kg/h.

In one embodiment, the spray-dryer unit in step b) is a rotary wheel type or a two-fluid nozzle atomizer.

In one embodiment, the spray-dryer unit in step b) is a rotary wheel type pressure-swirl single-fluid spray nozzle.

In one embodiment, the spray-dryer unit in step b) is a rotary wheel type atomizer.

In one embodiment, the spray-dryer unit in step b) is a rotary wheel type atomizer operated at 10000 to 30000 RPM. In one embodiment, the spray-dryer unit in step b) is a rotary wheel type atomizer operated at 10000 to 28000 RPM. In one embodiment, the spray-dryer unit in step b) is a rotary wheel type atomizer operated at 15000 to 25000 RPM or 20000 RPM, most particularly at 18000 to 20000 RPM.

In one embodiment, the rotary wheel type atomizer has a diameter of 100 mm and 24 holes.

In one embodiment, the spray-dryer unit in step b) is a two-fluid nozzle atomizer, such as, for example, an internal-mix two-fluid nozzle atomizer or an internal-mix two-fluid nozzle atomizer in co-current mode.

In one embodiment, the spray-dryer unit in step b) allows a water evaporation capacity of 5 to 30 kg/h.

In one embodiment, the spray-dryer unit in step b) is a GEA Niro Production Minor™ Spray Dryer from GEA Process Engineering (DK-2860 Soeborg).

In one embodiment, the two-fluid nozzle spray-dryer is operated in step c) using nitrogen as atomizing gas.

In one embodiment, the two-fluid nozzle spray-dryer is operated in step c) at an atomizing gas pressure of 0.5 to 3 bar. In another embodiment, the two-fluid nozzle spray-dryer is operated in step c) at an atomizing gas pressure of 1.5 to 3 bar. In another embodiment, the two-fluid nozzle spray-dryer is operated in step c) at an atomizing gas pressure of 1.5 to 2.6 bar. In still another embodiment, the two-fluid nozzle spray-dryer is operated in step c) at an atomizing gas pressure of or 2.2 to 2.6 bar. In yet another embodiment, the two-fluid nozzle spray-dryer is operated in step c) at an atomizing gas pressure of most particularly 2.3 to 2.5 bar.

In one embodiment, the drying gas in step d) is nitrogen.

In one embodiment, the drying gas in step d) is dry nitrogen with water content lower than about 100 ppm, for example, at a content lower than about 67 ppm.

In one embodiment, the drying gas in step d) is in the form of a gas stream.

In one embodiment, the nominal drying gas flow in step d) is 100 to 1000 kg/h. In another embodiment, the nominal drying gas flow in step d) is 300 to 600 kg/h. In another embodiment, the nominal drying gas flow in step d) is 350 to 450 kg/h. In still another embodiment, the nominal drying gas flow in step d) is 400 to 450 kg/h. In some embodiments, nominal drying gas flow in step d) is in closed cycle mode.

In one embodiment, the drying gas in step d) has an initial temperature of 150° C. to 200° C. In another embodiment, the drying gas in step d) has an initial temperature of 160° C. to 190° C. or 160° C. to 180° C. In another embodiment, the drying gas in step d) has an initial temperature of 170 to 180° C.

In one embodiment, the mixture of fine aqueous mist with drying gas in step d) has an outlet temperature of 70 to 150° C. In another embodiment, the mixture of fine aqueous mist with drying gas in step d) has an outlet temperature of 90° C. to 120° C. In still another embodiment, the mixture of fine aqueous mist with drying gas in step d) has an outlet temperature of 100° C. to 110° C.

In one embodiment, the temperature difference between the initial temperature of drying gas in step b) and the outlet temperature of the mixture of aqueous mist and drying gas in step d) is between 50° C. to 90° C. In one embodiment, the temperature difference between the initial temperature of drying gas in step b) and the outlet temperature of the mixture of aqueous mist and drying gas in step d) is between 60° C. to 80° C.

In one embodiment, the separation in step e) takes place in a cyclone.

In one embodiment, the separation in step e) takes place in a conical cyclone with flow rate 350 to 450 kg/h.

In a particular embodiment, the separation in step e) takes place in a cyclone with cut point of 5 μm to 10 μm.

In one embodiment, the amorphous ipatasertib monohydrochloride powder is transported in step e) from the drying chamber into a cyclone using a stream of drying gas.

In another embodiment, the amorphous ipatasertib monohydrochloride powder is collected in step f) by gravity into drums.

In one embodiment, the humidified drying gas in step h) is cooled to −10° C. to 20° C. In one embodiment, the humidified drying gas in step h) is cooled to 0° C. to 10° C. In another embodiment, the humidified drying gas in step h) is cooled to 5° C. to 9° C.

One exemplary embodiment of the process for the preparation of amorphous ipatasertib monohydrochloride is performed with process parameters as follows:

Feed solution: 20 to 25% (w/w) ipatasertib•HCl•EtOAc
   75 to 80% (w/w) water
Atomizer: rotary wheel type atomizer or two-fluid nozzle
Atomizer speed: 10000 to 28000 RPM in case of rotary wheel atomizer
Atomizing gas pressure: 2.2 to 2.6 bar in case of two-fluid nozzle
Drying gas inlet temperature: 160 to 180° C.
Drying gas outlet temperature: 90 to 120° C.
Drying gas (nitrogen): 450 kg/h, particularly in closed cycle mode
Condensing temperature (step h): 5 to 9° C.

In another exemplary embodiment of the process for the preparation of amorphous ipatasertib monohydrochloride is performed with process parameters as follows:

Feed solution composition: 20% (w/w) ipatasertib•HCl•EtOAc
   80% (w/w) purified water Atomizing mode: rotary wheel type atomizer or two-fluid nozzle
Atomizer speed: 19000 RPM in case of rotary wheel atomizer
Atomizing pressure: 2.4 bar in case of two-fluid nozzle
Drying gas inlet temperature: 175° C.
Drying gas outlet temperature: 105° C.
Drying gas (nitrogen): 400 kg/h, closed cycle mode
Condensing temperature: 5 to 9° C.

These conditions enable a yield of 90 to 94% as/is and of 96 to 100% "corrected".

Uses and Methods

Further provided herein are pharmaceutical compositions as defined above for use in the treatment of hyperproliferative disorders, particularly for the treatment of cancer.

Also provided herein are methods for the treatment of hyperproliferative disorders. In one embodiment is a method of treating hyperproliferative disorders comprising administering pharmaceutical compositions as described herein to a patient having such a hyperproliferative disorder. In one embodiment the hyperproliferative disorder is cancer.

In one embodiment, the cancer is a solid tumor. In one embodiment, the cancer is prostate cancer. In another embodiment, the cancer is breast cancer. In another embodiment, the cancer is lung cancer.

In another embodiment is the use of pharmaceutical compositions as defined above for the treatment of hyperproliferative disorders, particularly for the treatment of cancer.

EXAMPLES

The following examples 1-14 are provided for illustration. They should not be considered as limiting the scope of the invention, but merely as being representative thereof.

Example 1—Pharmaceutical Compositions of Ipatasertib•HCl

The following pharmaceutical compositions were prepared according to the flow diagram of FIG. 1 and following the detailed procedure below and the ingredient concentrations of the following Tables 1 to 7.

General procedure:
1) Sieving of the filler(s), (in case present) the moisture adsorbent and (in case present intragranular disintegrant) by passing through a mill (sieve size of 1.5 mm).
2) Preparing a pre-blend by mixing the filler(s) and (in case present) the moisture adsorbent together with the API followed by introduction of this pre-blend into a fluid-bed granulator (top-spray granulator in dry stage mode, Diosna Fluid Bed Dryer CCSP150, Diosna Dierks & Söhne GmbH, Osnabruck/DE).
3) Preparing a granulation solution by dissolving the binder in water at 25° C. followed by stirring until a clear solution is obtained.
4) Spraying of the granulation solution onto the fluidized pre-blend in the fluid-bed granulator to obtain wet granules (spray pressure 3 bar, spray rate of the granulation solution of 100 to 125 g/min, spray nozzle of 1.2 mm diameter).
5) Drying of the obtained wet granules in the fluid-bed granulator with air at 65° C. at an air flow of 360-560 $m^3$/h for 0-45 (mostly 15-30) minutes.
6) Sieving of the obtained granules by passing through a mill (sieve size of 1.5 mm).
7) Sieving of the extragranular disintegrant and (in case present) the glidant by passing through a mill (sieve size of 1.5 mm).
8) Preparing a first blend by mixing the extragranular disintegrant and (in case present) the glidant together with the dry granules in a blender.
9) Sieving of the lubricant by passing through a mill (sieve size of 1.5 mm).
10) Preparing a second blend by mixing the lubricant together with the first blend in a blender.
11) Compression of the second blend to tablets using a tablet press and punches (API content 100 mg: main compression force 10 kN; API content 200 mg: main compression force 14 kN.
12) If applicable, coating of the tablets in a pan coater, wherein an aqueous coating suspension comprising Opadry II 85F240172 PVA based film coat (pink) is sprayed on the tablet using a spray nozzle of 1.2 mm diameter at a spray pressure of 2 to 2.5 bar.
13) If applicable, drying of the film coated tablet (fct) using air at an inlet temperature of 60° C., and at an inlet flow of 450 $m^3$/h.

TABLE 1

Ingredients of Compositions 1 to 5 (uncoated tablets).

| Ingredients | Comp. 1 GPV0006/03 [%] | Comp. 2 GPV0011/03 [%] | Comp. 3 Batch no. GPV0004/09 [%] | Comp. 4 GPV0004/10 [%] | Comp. 5 GPV0004/07 [%] |
|---|---|---|---|---|---|
| Intragranular | | | | | |
| Ipatasertib•HCl | 32.23 | 30.85 | 30.00 | 30.00 | 30.00 |
| Microcrystalline Cellulose, Type PH-101 | 36.27 | 37.65 | 38.50 | 38.50 | 56.50 |
| Pregelatinized starch | 12.00 | 12.00 | — | — | — |
| Lactose | 6.00 | 6.00 | — | — | — |
| Mannitol | — | — | 18.00 | — | — |
| Corn starch | — | — | — | 18.00 | — |
| Colloidal silicon dioxide | 4.00 | 4.00 | 5.00 | 5.00 | 5.00 |
| Povidone K90 | 2.50 | 2.50 | 2.50 | — | 2.50 |
| Povidone K30 | — | — | — | 2.50 | — |
| Croscarmellose sodium | — | 2.50 | 2.50 | 2.50 | 2.50 |

TABLE 1-continued

Ingredients of Compositions 1 to 5 (uncoated tablets).

| Ingredients | Comp. 1 GPV0006/03 [%] | Comp. 2 GPV0011/03 [%] | Comp. 3 GPV0004/09 [%] | Comp. 4 GPV0004/10 [%] | Comp. 5 GPV0004/07 [%] |
|---|---|---|---|---|---|
| Batch no. | | | | | |
| Extragranular | | | | | |
| Croscarmellose sodium | 5.00 | 2.50 | 2.50 | 2.50 | 2.50 |
| Colloidal silicon dioxide | 1.00 | 1.00 | 1.00 | 1.00 | — |
| Magnesium stearate | 1.00 | 1.00 | 1.00 | 1.00 | 1.00 |
| Tablet Mass | 670 mg | 700 mg | 667 mg | 667 mg | 667 mg |

TABLE 2

Ingredients of Composition 6 (film coated tablet).

Composition 6
Batch no.
GMP0132

| Ingredients | [%] | mg/tablet |
|---|---|---|
| Intragranular | | |
| Ipatasertib•HCl (relating to 100 mg free base) | 30.85 | 107.97 |
| Microcrystalline Cellulose (Avicel PH101) | 43.65 | 152.78 |
| Pregelatinized Starch, Type 1500 (Starxx 1500) | 12 | 42 |
| Colloidal Silica (Aerosil 200 Pharma) | 3 | 10.5 |
| Polyvinylpyrrolidone K90 (Kollidon K90) | 2.5 | 8.75 |
| Total | 92 | 322 |
| Extragranular | | |
| Colloidal Silicone Dioxide (Aerosil 200 Pharma) | 1 | 3.5 |
| Croscarmellose Sodium non-GMO (Disolcel GF) | 6 | 21 |
| Mg-Stearate | 1 | 3.5 |
| Total | 8 | 38.5 |
| Total (tablet core) | 100 | 350 |
| Film coating | | |
| Opadry II 85F220169 PVA based film coat (yellow) | — | 15 |
| Total (fct) | | 365 |

TABLE 3

Ingredients of Composition 7 (film coated tablet).

Composition 7
Batch no.
GMP0147/03

| Ingredients | [%] | mg/tablet |
|---|---|---|
| Intragranular | | |
| Ipatasertib•HCl (relating to 200 mg free base) | 30.85 | 215.94 |
| Microcrystalline Cellulose (Avicel PH101) | 43.65 | 305.56 |
| Pregelatinized Starch, Type 1500 (Starxx 1500) | 12 | 84 |
| Colloidal Silica (Aerosil 200 Pharma) | 3 | 21 |
| Polyvinylpyrrolidone K90 (Kollidon K90) | 2.5 | 17.5 |
| Total | 92 | 644 |
| Extragranular | | |
| Colloidal Silicone Dioxide (Aerosil 200 Pharma) | 1 | 7 |
| Croscarmellose Sodium non-GMO (Disolcel GF) | 6 | 42 |
| Mg-Stearate | 1 | 7 |
| Total | 8 | 56 |
| Total (tablet core) | 100 | 700 |
| Film coating | | |
| Opadry II 85F240172 PVA based film coat (pink) | — | 25 |
| Total (fct) | | 725 |

TABLE 4

Ingredients of Composition 8 (film coated tablet).

| | Composition 8 Batch no. GPV0028/04 | |
|---|---|---|
| Ingredients | [%] | mg/tablet |
| Intragranular | | |
| Ipatasertib•HCl (relating to 200 mg free base) | 30.85 | 215.92 |
| Microcrystalline Cellulose (Avicel PH101) | 43.65 | 305.58 |
| Pregelatinized Starch, Type 1500 (Starxx 1500) | 12 | 84 |
| Colloidal Silica (Aerosil 200 Pharma) | 3 | 21 |
| Croscarmellose Sodium (Disolcel GF) | 2.5 | 17.5 |
| Polyvinylpyrrolidone K90 (Kollidon K90) | 2.5 | 17.5 |
| Total | 94.5 | 661.5 |
| Extragranular | | |
| Colloidal Silicone Dioxide (Aerosil 200 Pharma) | 1 | 7 |
| Croscarmellose Sodium (Disolcel GF) | 3.5 | 24.5 |
| Mg-Stearate | 1 | 7 |
| Total | 5.5 | 38.5 |
| Total (tablet core) | 100 | 700 |
| Film coating | | |
| Opadry II PVA based film coat | — | 20 |
| Total (fct) | | 720 |

TABLE 5

Ingredients of Compositions 9 and 10 (uncoated tablets) and lamination properties thereof.

| | Comp. 9 | Comp. 10 |
|---|---|---|
| | Batch no. | |
| | GPV0004/13 | GPV0011/03 |
| Ingredients | [%] | [%] |
| Intragranular | | |
| Ipatasertib•HCl | 30 | 30 |
| Microcrystalline Cellulose, Type PH-101 | 46.5 | 28.5 |
| Pregelatinized starch | — | — |
| Lactose | — | 18 |
| Mannitol | — | — |
| Corn starch | — | — |
| Colloidal silicon dioxide | 5 | 5 |
| Povidone K90 | 1.5 | 2.5 |
| Povidone K30 | — | — |
| Croscarmellose sodium | 2.5 | 2.5 |
| Extragranular | | |
| Microcrystalline Cellulose, Type PH-102 | 11 | 10 |
| Croscarmellose sodium | 2.5 | 2.5 |
| Colloidal silicon dioxide | — | — |
| Magnesium stearate | 1 | 1 |
| Total | 100% | 100% |
| Tablet Mass | 667 mg | 667 mg |

| | # tablets laminating/ # tablets tested | # tablets laminating/ # tablets tested |
|---|---|---|
| Compression force 14 kN | 2/10 | 4/10 |
| Compression force 16 kN | 9/10 | 8/10 |
| Compression force 18.10 kN | 2/10 | 7/10 |
| Compression force 19.90 kN | 3/7 | 10/10 |

TABLE 6

Ingredients of Compositions 11 to 13 (uncoated tablets) and analytical properties thereof.

| | Comp. 11 | Comp. 12 | Comp. 13 |
|---|---|---|---|
| | Batch no. | | |
| | GPV0004/04 | GPV0004/05 | GPV0004/06 |
| Ingredients | [%] | [%] | [%] |
| Intragranular | | | |
| Ipatasertib•HCl | 30 | 30 | 30 |
| Microcrystalline Cellulose, Type PH-101 | 54 | 59 | 56.50 |
| Pregelatinized starch | — | — | — |
| Lactose | — | — | — |
| Mannitol | — | — | — |
| Corn starch | — | — | — |
| Colloidal silicon dioxide | 5 | 0 | 5 |
| Povidone K90 | — | — | — |
| Povidone K30 | 5 | 5 | 2.5 |
| Croscarmellose sodium | 2.5 | 2.5 | 2.5 |
| Extragranular | | | |
| Microcrystalline Cellulose, Type PH-102 | — | — | — |
| Croscarmellose sodium | 2.5 | 2.5 | 2.5 |
| Colloidal silicon dioxide | — | — | — |
| Magnesium stearate | 1 | 1 | 1 |
| Total | 100% | 100% | 100% |
| Tablet Mass | 667 mg | 667 mg | 667 mg |
| Granulate PSD (d') | 197 μm | 285 μm | |
| % fines (<90 um) | 25.5% | 16.9% | |
| Bulk density (gcm$^{-3}$) | 0.25 | 0.21 | |
| Disintegration time (min:sec) | 12:42 (236N) | 14:43 (199N) | |

TABLE 7

Ingredients of Compositions 14 and 15 (uncoated tablets). The intragranular matrix of Composition 8 (GPV0028/04) is constituted identically but granules are passed through a mill of sieve size of 1.5 mm in process step 6) according to the general procedure.

| | Comp. 14 | | Comp. 15 | |
|---|---|---|---|---|
| | Batch no. | | | |
| | GPV0028/06 | | GPV0028/07 | |
| Ingredients | [%] | mg/tablet | [%] | mg/tablet |
| Intragranular | | | | |
| Ipatasertib•HCl (relating to 200 mg free base) | 30.85 | 215.92 | 30.85 | 215.92 |
| Microcrystalline Cellulose (Avicel PH101) | 43.65 | 305.58 | 43.65 | 305.58 |
| Pregelatinized Starch, Type 1500 (Starxx 1500) | 12 | 84 | 12 | 84 |
| Colloidal Silica (Aerosil 200 Pharma) | 3 | 21 | 3 | 21 |
| Croscarmellose Sodium (Disolcel GF) | 2.5 | 17.5 | 2.5 | 17.5 |
| Polyvinylpyrrolidone K90 (Kollidon K90) | 2.5 | 17.5 | 2.5 | 17.5 |
| Total | 94.5 | 661.5 | 94.5 | 661.5 |
| Sieve size of mill in process step 6 | 2.0 mm | | 2.0 mm and 0.8 mm | |
| Extragranular | | | | |
| Colloidal Silicone Dioxide (Aerosil 200 Pharma) | 1 | 7 | 1 | 7 |
| Croscarmellose Sodium (Disolcel GF) | 3.25 | 22.75 | 3.75 | 26.25 |
| Mg-Stearate | 1.25 | 8.75 | 0.75 | 5.25 |
| Total | 5.5 | 38.5 | 5.5 | 38.5 |
| Total (tablet core) | 100 | 700 | 100 | 700 |

Example 2—Impact of Filler on Pharmaceutical Compositions Comprising Ipatasertib•HCl Tablet hardness was measured by compressing tablets at different compression forces (8-24 kN, every 2 kN). At each compression force, ten tablets were tested in a tablet hardness tester (Sotax AG, Aesch/CH) and the resulting breaking forces were recorded and averaged. Each point in the FIG. 2 represents the average hardness of n=10 tablets at the respective compression force.

Figure 2:
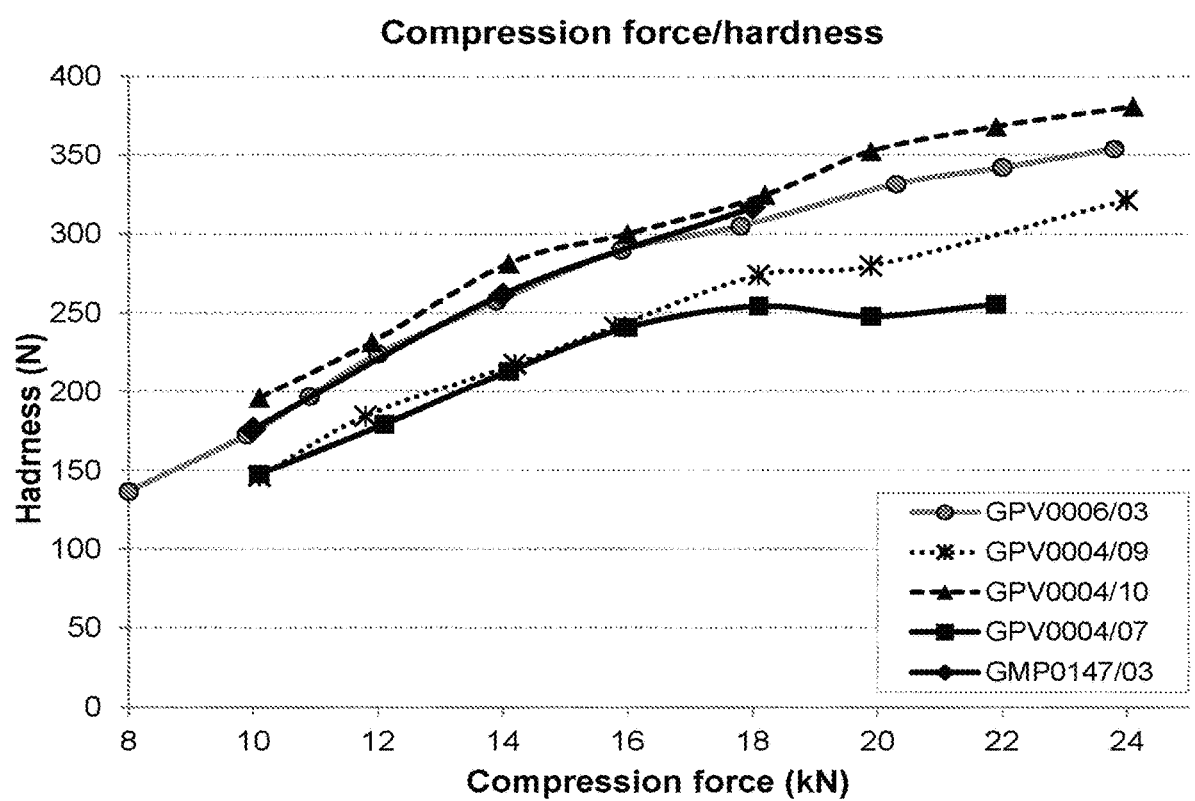
FIG. 2 illustrates the impact of filler on tablet hardness dependent on compression force.

FIG. 2 provides compression force/hardness curves of five exemplary tablet cores:
  GPV0006/03 corresponds to Composition 1 comprising 36.27% wt microcrystalline celluose, 12.00% wt pregelatinized starch and 6.00% wt lactose as fillers (weight ratio 6:2:1).
  GPV0004/09 corresponds to Composition 3 comprising 38.50% wt microcrystalline celluose and 18.00% wt mannitol as fillers (weight ratio about 2:1).
  GPV0004/10 corresponds to Composition 4 comprising 38.50% wt microcrystalline celluose and 18.00% wt corn starch as fillers (weight ratio about 2:1).
  GPV0004/07 corresponds to Composition 5 comprising 56.50% wt microcrystalline celluose as single filler.
  GMP0147/03 corresponds to Composition 7 comprising 43.65% wt microcrystalline celluose and 12.00% wt pregelatinized starch as fillers (weight ratio about 78:22).

Ideally, a tablet hardness between 200N to 350N is achieved at compression forces of 12 to 20 kN (depending on particle size and punch type). Therefore, a less steep compression force/hardness profile is preferred. For example, compositions 1, 3, 4 and 7 described herein can meet this force. Microcrystalline cellulose (Avicel PH101) as filler favorably compensates the brittle properties of ipatasertib•HCl. Microcrystalline cellulose as filler alone (such as in Composition 5) does not yield an appropriate compression behavior, as compression force/hardness profiles are very steep.

It has been further found, that the combination of microcrystalline cellulose and pregelatinized starch (Starxx 1500), such as Composition 7, as fillers together with ipatasertib•HCl provide a composition with improved fluid bed granulation process performance due to the water absorbing properties of pregelatinized starch and also due to an improved compression performance as compared to compositions comprising microcrystalline cellulose as filler alone.

It has been further found that mannitol as filler (such as in Composition 3), can in some instances be less suitable since tablets obtained with mannitol as filler can use very high ejection forces from the tablet press, indicating potential tablet robustness issues (e.g. sticking during tablet compression).

It has been further found that corn starch as filler (such as in Composition 4) can be less beneficial since corn starch has intrinsic elastic mechanical properties which can increase the risk of tablet lamination.

It has been further found that lactose as filler (such as Composition 12) can be less beneficial since tablets obtained with lactose as filler can exhibit increased dissolution times. Lactose also has intrinsic brittle mechanical properties which can increase the risk for tablet lamination. The combination of microcrystalline cellulose and lactose as fillers can increase the risk of tablet lamination as is evidenced by the data provided at the bottom of Table 5.

Tablet lamination of the tablets was tested in a standard tablet hardness tester. For each compression force 10 tablets were tested and the tablet breaking direction was visually observed. Tablets without lamination appeared to exhibit a vertical breaking direction. The number of tablets exhibiting a horizontal breaking direction (indicating lamination) was recorded.

The combination of microcrystalline cellulose and pregelatinized starch as fillers showed good granulation process robustness, resulted in acceptable compression force/hardness profiles with appropriate low tablet abrasion at lower hardness, and also yielded acceptable disintegration times at higher hardness.

Example 3—Impact of Moisture Adsorbent on Pharmaceutical Compositions Comprising Ipatasertib•HCl Compositions 11 and 12 were prepared to assess the impact of moisture absorbent. Granules could be obtained with and without intragranular colloidal silica as moisture absorbent. But the granulation process without colloidal silica as moisture absorbent appeared to be less robust, i.e. granulates seemed more sensitive to higher spray rates. As can be seen from Table 6, granules without intragranular colloidal silica (e.g. Comp. 12: d'=285 μm, 16.9% fines) exhibited a significantly increased PSD d' (+45%) and decreased fines content (−51%) in comparison to granules comprising 5% wt colloidal silica (e.g. Comp. 11: d'=197 μm, 25.5% fines). The elimination of intragranular colloidal silica resulted in lower tablet hardness and higher tablet abrasion. Granules without colloidal silica exhibit a 15% higher disintegration time (Comp. 12: 14 min 43 sec; Comp. 11: 12 min 42 sec) despite the lower hardness of tablets.

Colloidal silica appeared to have only a marginal effect on bulk density (Comp. 12: 0.21 gcm$^{-3}$; Comp. 11: 0.25 gcm$^{-3}$).

Figure 3:
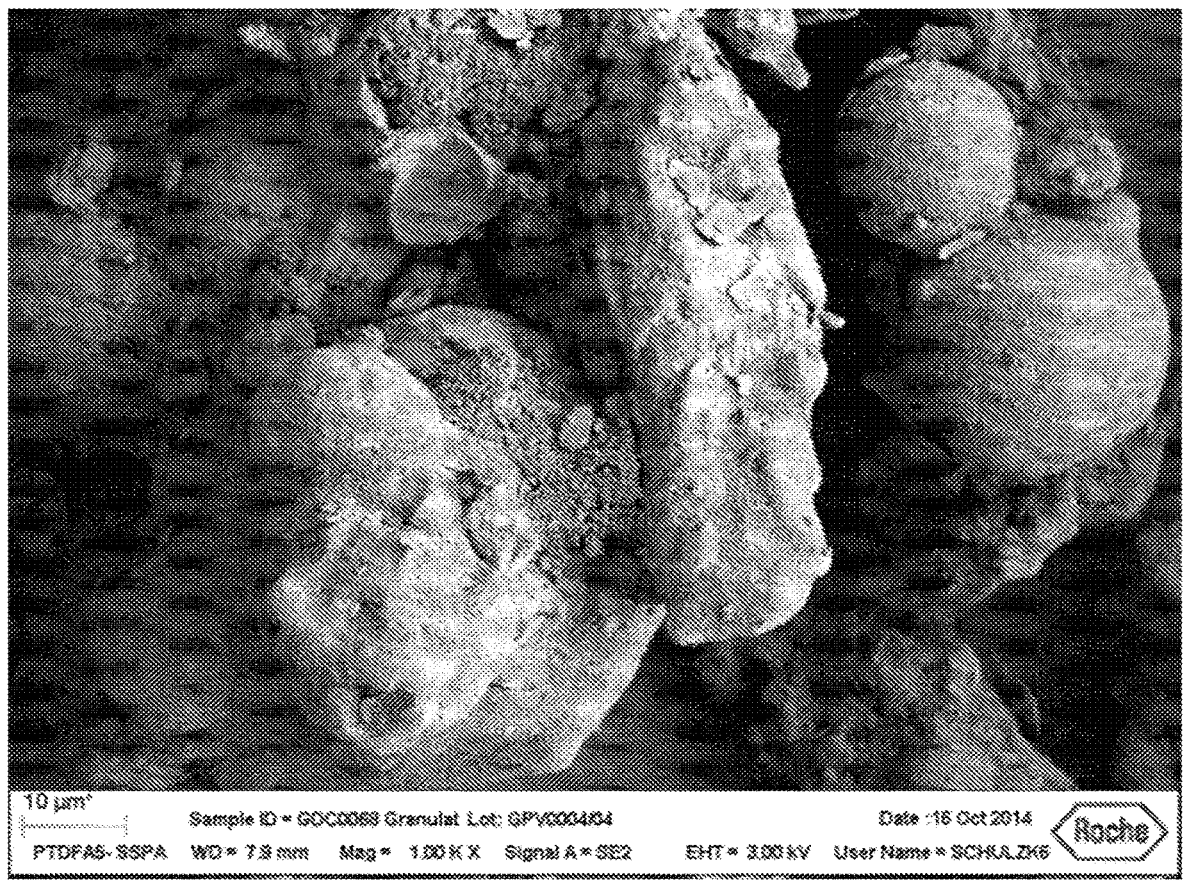
FIG. 3 illustrates a Scanning Electron Micrograph (SEM) of granules of Composition 11 comprising colloidal silica.

FIG. 3 provides a Scanning Electron Micrograph obtained from Composition 11. Round particles (amorphous API) are visible which are layered with colloidal silica (small dots on round particles).

Figure 4:
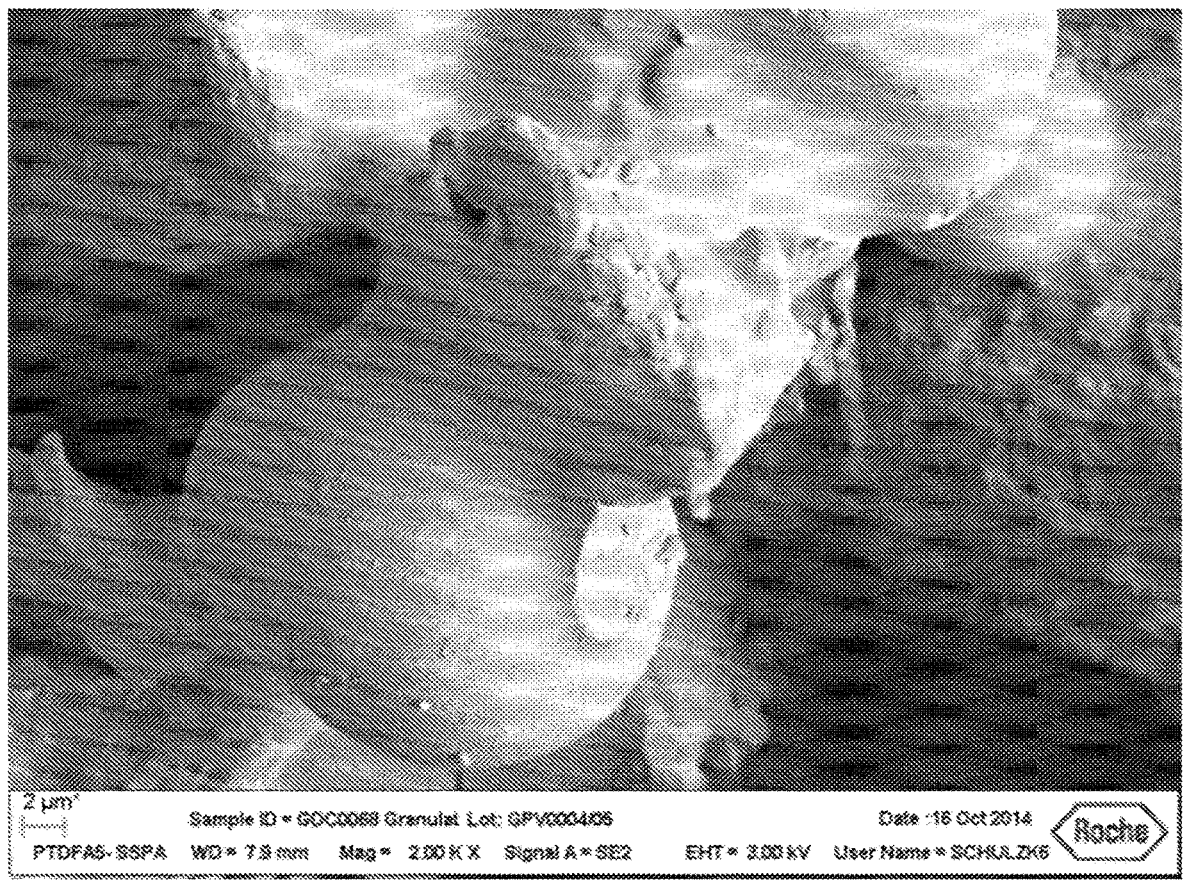
FIG. 4 illustrates a Scanning Electron Micrograph (SEM) obtained from granules of Composition 12 devoid of colloidal silica.

FIG. 4 provides a Scanning Electron Micrograph obtained from Composition 12. The roundish API particles are fused with the other excipients' matrix. Due the API's high water solubility, the API is assumed to be dissolved during granulation and to be precipitated together with the other excipients.

Colloidal Silica (Aerosil 200 Pharma) as intragranular moisture absorbent supports a robust fluid bed granulation process performance.

Figure 5:
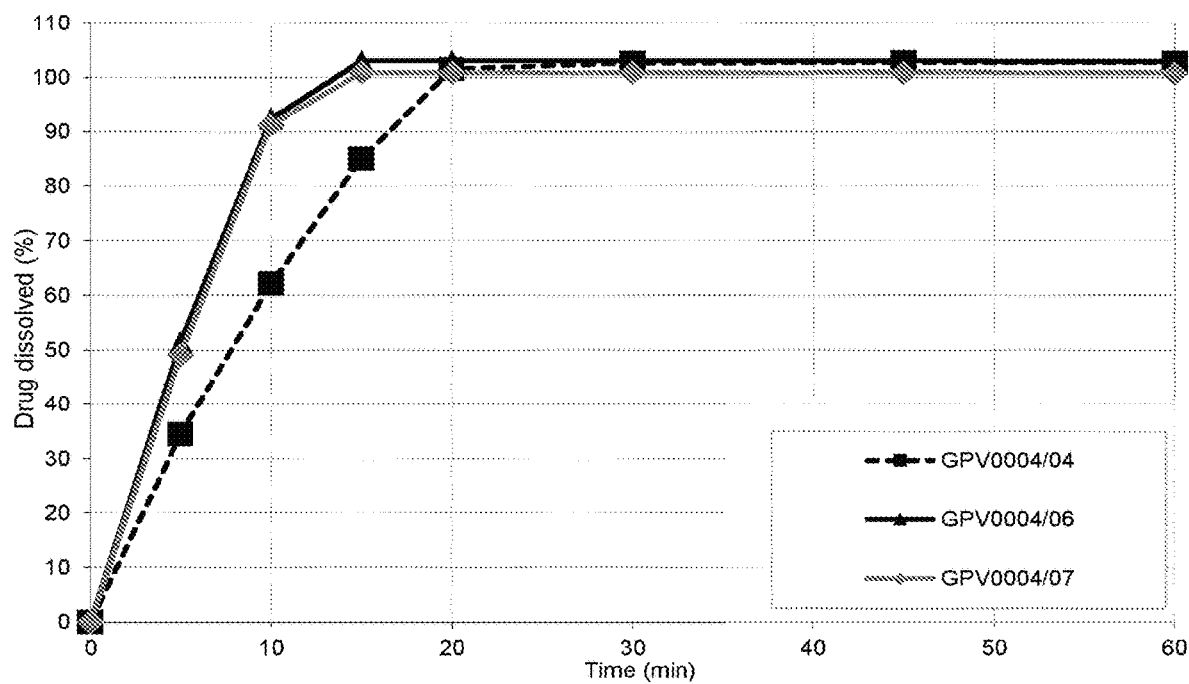
FIG. 5 illustrates the impact of binder grade on drug dissolution time.

Example 4—Impact of Binder on Pharmaceutical Compositions Comprising Ipatasertib•HCl Particle size, bulk density and disintegration time of three tablets (Composition 11, 13 and 5) were investigated as presented in Table 8. FIG. 5 provides drug dissolution profiles of these three compositions.

TABLE 8

Analytical properties of compositions 11, 13 and 5.

| Composition | Binder | Granulate PSD (d') | % fines (<90 um) | Bulk density (gcm$^{-3}$) | Disintegration time (min:sec) |
|---|---|---|---|---|---|
| Comp. 11, GPV0004/04 | 5% PVP K30 | 197 μm | 25.5 | 0.25 | 12:42 (236N) |
| Comp. 13, GPV0004/06 | 2.5% PVP K30 | 195 μm | 18.9 | 0.2 | 9:45 (249N) |
| Comp. 5, GPV0004/07 | 2.5% PVP K90 | 336 μm | 7.6 | 0.19 | 13:18 (256N) |

In Compositions 11 and 13, another binder grade was used (PVP K30) having less binding capacity as compared to Composition 5 (PVP K90). Similar process robustness was observed for all three compositions but the particle size distribution was shifted to smaller sizes and higher amount of fine particles for compositions comprising PVP K 30 as binder.

2.5% PVP K90 resulted in a larger granule particle size as compared to 2.5% and 5% PVP K30. Furthermore, the amount of fine fraction (fines) in the granules could be substantially reduce by using PVP K90 as compared to PVP K30, which is considered beneficial to reduce the risk of tablet lamination Impact of binder grade on tablet disintegration time and drug dissolution was not significant. At similar compression force used for tableting (approx. 16 kN), the data show that PVP K90 (Composition 5) leads to similar dissolution performance from the tablets than PVP K30 (Compositions 11 and 13) as can be seen in FIG. 5.

PVP K90 appears to lead to larger granules and reduced fines content while maintaining the same beneficial dissolution performance at comparable hardness. Polyvinylpyrrolidone K90 (Kollidon K90) as binder facilitates the formation of appropriate granule particle size disctribution for a robust downstream process performance.

Example 5—Impact of Lubricant on Pharmaceutical Compositions Comprising Ipatasertib•HCl A lubricant has the purpose to lubrify the tablet compression tooling to support a robust tablet compression process. Two tablets were prepared according to the method provided in Example 1 to investigate the impact of lubricant on robustness of tablet compression performance:

Contrary to Example 1, the intragranular matrix of Composition 14 was sieved in step 6 of the general procedure through a sieve of 2.0 mm to obtain coarse granules.

Contrary to Example 1, the intragranular matrix of Composition 15 was sieved in step 6 of the general procedure through a sieve of 2.0 mm and through a sieve of 0.8 mm to obtain fine granules.

Particle size distribution of such obtained granules were subsequently investigated prior to mixing with the extragranular matrix as provided in Table 9.

TABLE 9

Analytical properties of the granules of Compositions 14 and 15 after milling in process step 6).

| Composition | d' | % fines <90 μm | % fines <125 μm |
|---|---|---|---|
| Comp. 14 GPV0028/06 | 290 μm | 11.8 | 20.0 |
| Comp. 15 GPV0028/07 | 241 μm | 15.1 | 27.0 |

Composition 14 can be considered an example of over-lubricated final blend since coarse granules with hence smaller surface area were combined with a Magnesium stearate concentration above target.

Composition 15 can be considered an example of under-lubricated final blend since fine granules with hence larger surface area were combined with a Magnesium stearate concentration below target.

Tablet compression performance, i.e. sticking and lamination behavior, was subsequently assessed of Compositions 14 and 15. Throughout all compression runs ejection force was considered to be in a normal range for both 100 mg (100-130N) and 200 mg (~200N) tablet sizes, no increase was observed. Interestingly, both examples revealed robust tablet compression performance showing low risk of sticking and lamination. The robust tablet compression and the absence of microcracks (as confirmed by μCT imaging) suggest that 1% wt of Magnesium stearate corresponds to an optimal lubricant concentration in the extragranular matrix for both the 100 mg and 200 mg tablet dose strengths.

Example 6—Amorphous Ipatasertib Monohydrochloride Prepared Using Two-Fluid Nozzle Spray-Dryer WO2013/173811A1 describes on pages 33-35 (Ex. 12A-12C) a number of spray drying processes to manufacture amorphous ipatasertib monohydrochloride. Amorphous ipatasertib monohydrochloride was prepared by spray drying solutions of different educt forms of ipatasertib monohydrochloride using a two-fluid nozzle spray-dryer. The conditions and results are shown below in Table 10.

TABLE 10

Process parameters and quality attributes of amorphous ipatasertib monohydrochloride.

| | Example number | | |
|---|---|---|---|
| | 6A | 6B | 6C |
| Batch | 06MG68.HQ00001 | 06MG68.HQ00002 | 06MG68.HQ00003 |
| Loop | Open | Open | Open |
| Feed composition | | | |
| Starting material | ipatasertib•HCl•EtOAc | ipatasertib•HCl | ipatasertib•HCl•EtOAc |
| Process solvent | ethanol | ethanol | water |
| Feed properties | | | |
| Total starting material [g]$^a$ | 50.0 | 50.0 | 25.0 |
| Total process solvent [g]$^a$ | 250.0 | 250.0 | 100.0 |
| Feed solution [g] | 300.0 | 300.0 | 125.0 |
| C_feed [%w/w] | 16.7 | 16.7 | 20.0 |
| Spray drying parameters | | | |
| Drying gas T_in [° C.] | 120 ± 1 | 119 ± 1 | 154 ± 1 |
| Drying gas T_out [° C.] | 69 ± 1 | 69 ± 1 | 90 ± 1 |
| F_feed [ml/min] | 15 | 15 | 5 |
| Rotamer level [mm] | 40 | 40 | 40 |
| Drying time [min] | 23 | 23 | 23 |
| Process yield | | | |
| Yield [g] | 28.8 | 48.4 | 15.0 |
| Yield as/is [%]$^b$ | 58 | 97 | 60 |
| Yield corrected [%]$^b$ | 90 | 97 | 93 |
| Analytical results | | | |
| Water content [% w/w] | 0.89 | 0.43 | 1.02 |
| Ethanol [% w/w] | 2.19 | 2.78 | 0.01 |
| Ethyl acetate [% w/w] | 0.25 | 0.01 | 0.23 |
| Purity (HPLC) [% area] | 99.93 | 99.92 | 99.93 |

The material obtained according to Table 10 was further investigated with additional analytical methods. Results obtained for the materials as described in WO2013/173811A1 in Examples 12 A-C are described below in Table 11 and Table 12.

TABLE 11

Quality attributes of amorphous ipatasertib monohydrochloride.

| | Example number | | | |
|---|---|---|---|---|
| | 6A' (prepared analogous to 6A) | 6B' (prepared analogous to 6B) | 6C | 6C' (prepared analogous to 6C) |
| Batch | step 4A-854924 | step 3-854917 | 06MG68.HQ00003 | 06MG68.HQ00010 |
| Starting material | ipatasertib•HCl•EtOAc | ipatasertib•HCl | ipatasertib•HCl•EtOAc | ipatasertib•HCl•EtOAc |
| Process solvent | ethanol | ethanol | water | water |
| HPLC purity | No imp > 0.05% | No imp > 0.05% | No imp > 0.05% | No imp > 0.05% |
| Assay (w/w %) | 100.2 | 99.6 | 99.5 | 99.7 |
| Chloride eq | 1.0 | 1.0 | 0.97 | 1.0 |

TABLE 11-continued

Quality attributes of amorphous ipatasertib monohydrochloride.

| | Example number | | | |
|---|---|---|---|---|
| | 6A' (prepared analogous to 6A) | 6B' (prepared analogous to 6B) | 6C | 6C' (prepared analogous to 6C) |
| Water Content (w/w %) | 1.3 | 1.4 | 1.3 | 1.6 |
| Residual solvents | | | | |
| EtOH (w/w %) | 0.6 | 0.7 | ND | ND |
| EtOAC (w/w %) | 0.1 | ND | 0.02 | 0.2 |
| XRPD | amorphous | amorphous | amorphous | ND |
| Glass Transition tg (° C.) | 131 | 132 | 131 | ND |
| PSD | | | | |
| $d_{10}$ (μm) | 0.7 | 0.7 | 0.7 | 0.8 |
| $d_{50}$ (μm) | 3.8 | 5.2 | 4.3 | 3.0 |
| $d_{90}$ (μm) | 7.5 | 10.8 | 8.1 | 5.7 |
| Bulk density (gcm$^{-3}$) | | | | 0.26 |
| Tapped density (gcm$^{-3}$) | | | | 0.42 |
| Carr Index (%) | | | | 38 |

(ND = not determined)

TABLE 12

Shear cell testing of amorphous ipatasertib monohydrochloride of Example 6C' (Batch HQ00010) as measured using an automated Ring Shear Tester RST-XS (Dr. Dietmar Schulze Schüttgutmesstechnik, Wolfenbüttel, DE).

| Pre-shear stress [PA] | tc [Pa] | Consolidation stress (σ1) [PA] | Flow Function Constant (ffc) |
|---|---|---|---|
| 1000 | 514 | 2118 | 1.08 |
| 2000 | 1095 | 4844 | 1.09 |
| 4000 | 2041 | 9557 | 1.12 |

Figure 6:
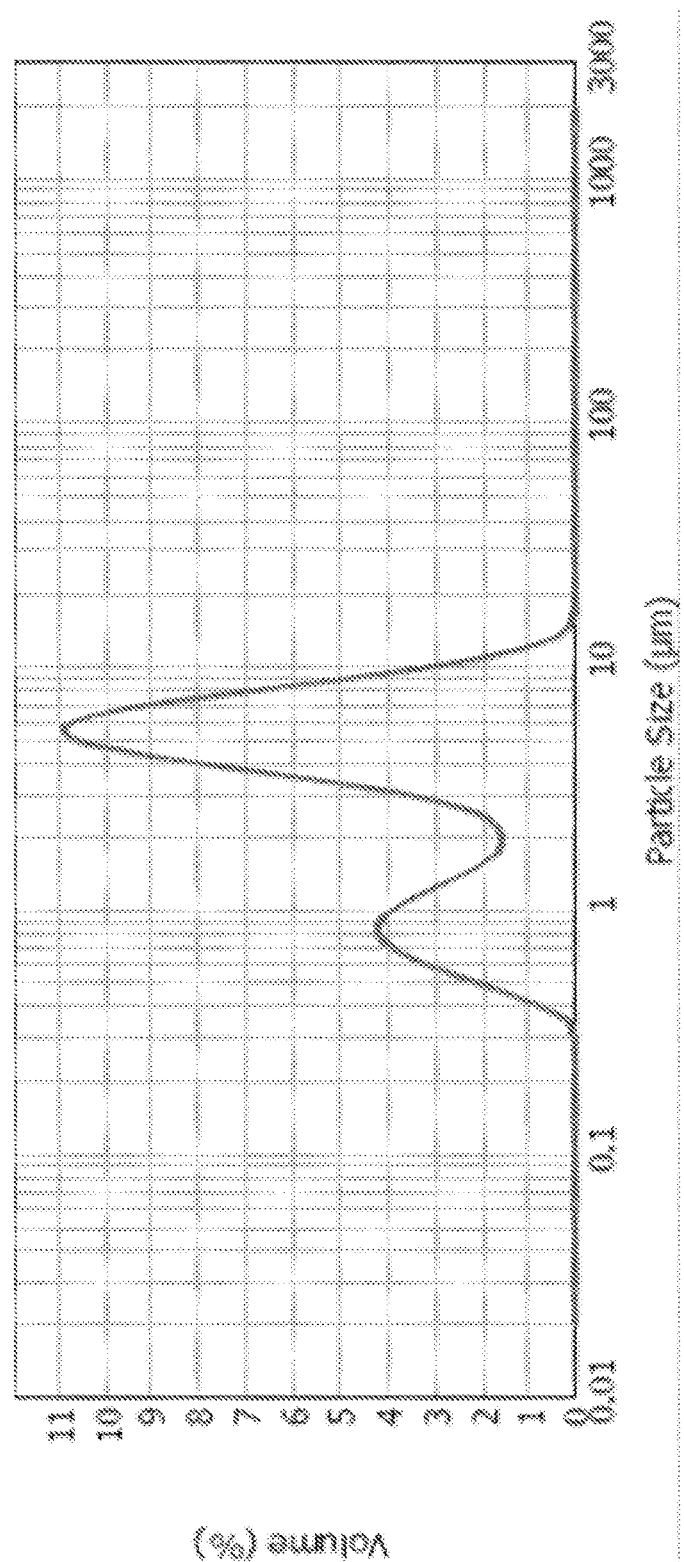
FIG. 6 illustrates particle size distribution of the material of Example 6C (Batch HQ00003) spray dried with two-feed nozzle as obtained by laser diffraction A bimodal particle size distribution is obvious.
Figure 7:
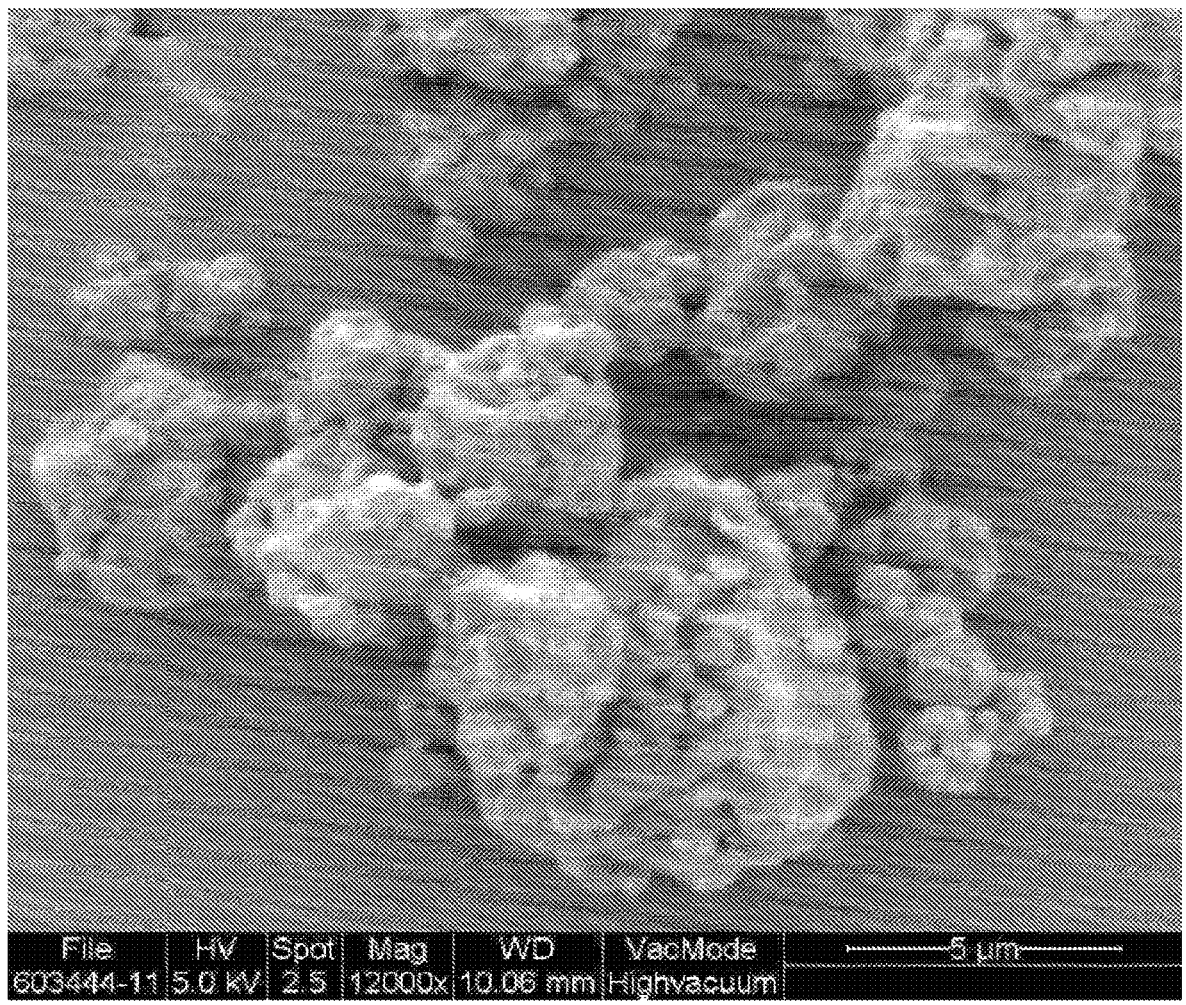
FIG. 7 illustrates a SEM micrograph of the material of Example 6C (Batch HQ00003) spray dried with two-feed nozzle. A bimodal particle size distribution of nanoparticles and particles of 1-10 μm diameter is obviouos. Sample was sputtered with gold.

The following results were obtained from analytical investigation of the materials according to Examples 6A, 6A', 6B, 6B', 6C and 6C' which were obtained as described in WO2013/173811A1 on pages 33-35:
  The bulk density of the powder of Example 6C' is 0.262 gcm$^{-3}$; the tapped density is 0.423 gcm$^{-3}$, leading to a Carr index of 38%, indicating a very poorly flowing material.
  Shear cell testing (ffc around 1.1 across all pre-shear stresses, see Table 12) indicates that the powder has very poor flowability. The shear testing show that the poor flow is primarily due to the small particle size and large cohesion (high cohesiveness) of particles, despite the round morphology of the particles.
  Particle size analysis of the powder of Example 6C has revealed a bimodal particle size distribution with $d_{90}$ below 8.1 μm (see FIG. 6).
  According to optical microscopy and scanning electron microscopy (see FIG. 7) the material obtained of the powder of Example 6C consists of roundish particles of two size ranges: sub-micron sized nanoparticles nanoparticles and particles of 1-10 μm diameter.

Figure 8:
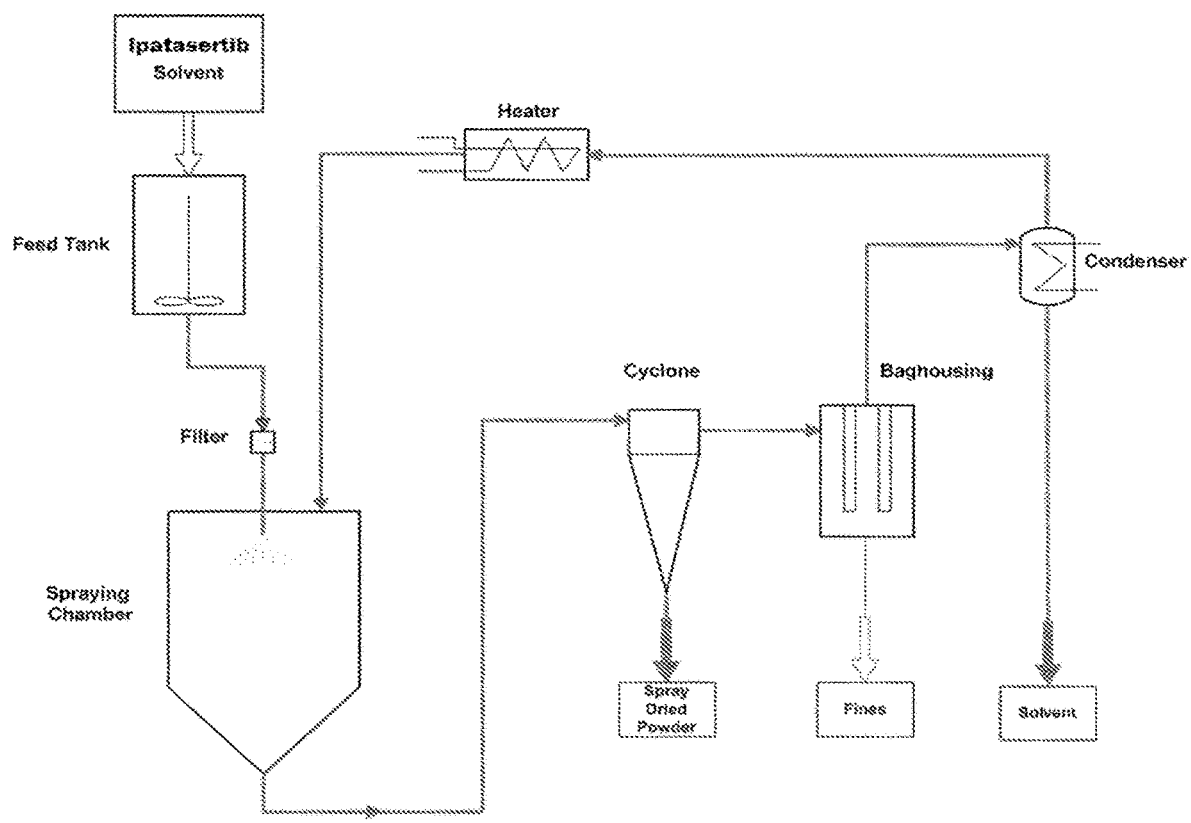
FIG. 8 illustrates a flow diagram of spray drying process according to the general procedure of Example 7.
Figure 9:
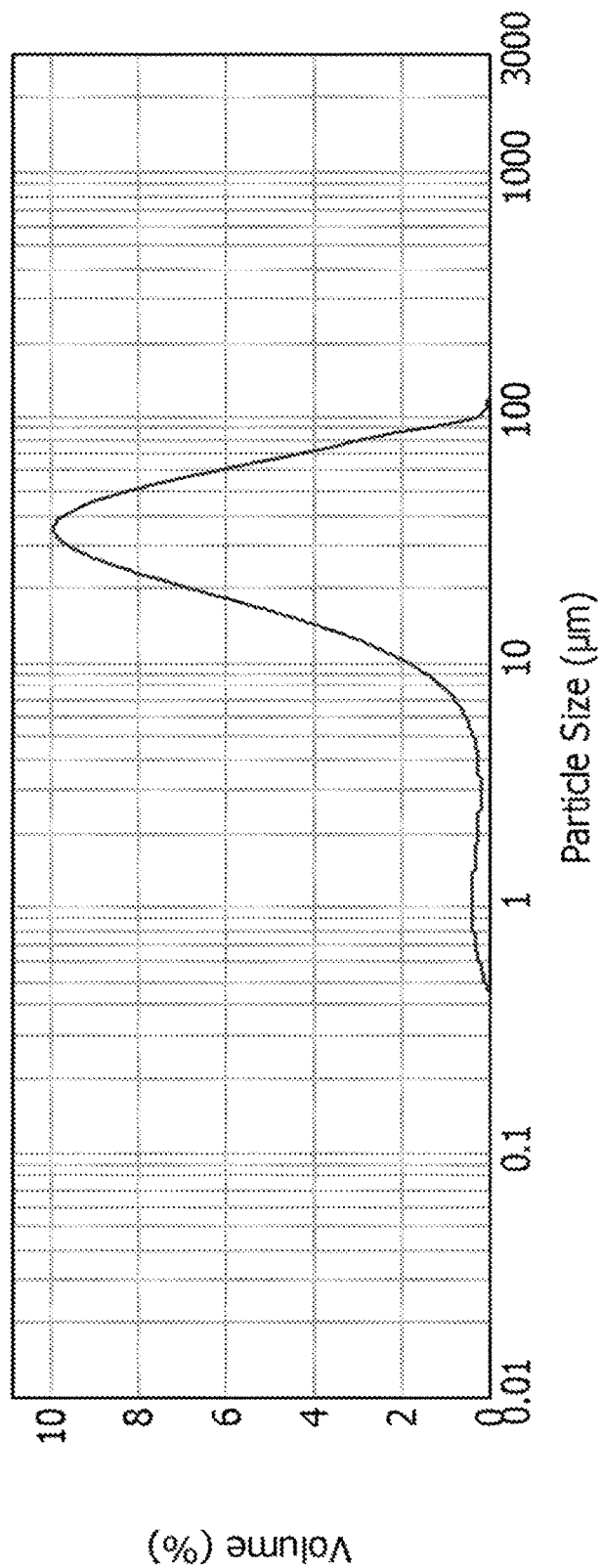
FIG. 9 illustrates particle size distribution of spray dried material with rotary wheel nozzle, i.e. of the material of batch BS1506SA03 of Example 13 (Table 20) obtained using a Malvern Mastersizer 2000 equipped with Hydro 2000S wet sanple dispersion unit (Malvern Instruments Ltd, Malvern/UK). A monomodal particle size distribution is obvious.
Figure 10:
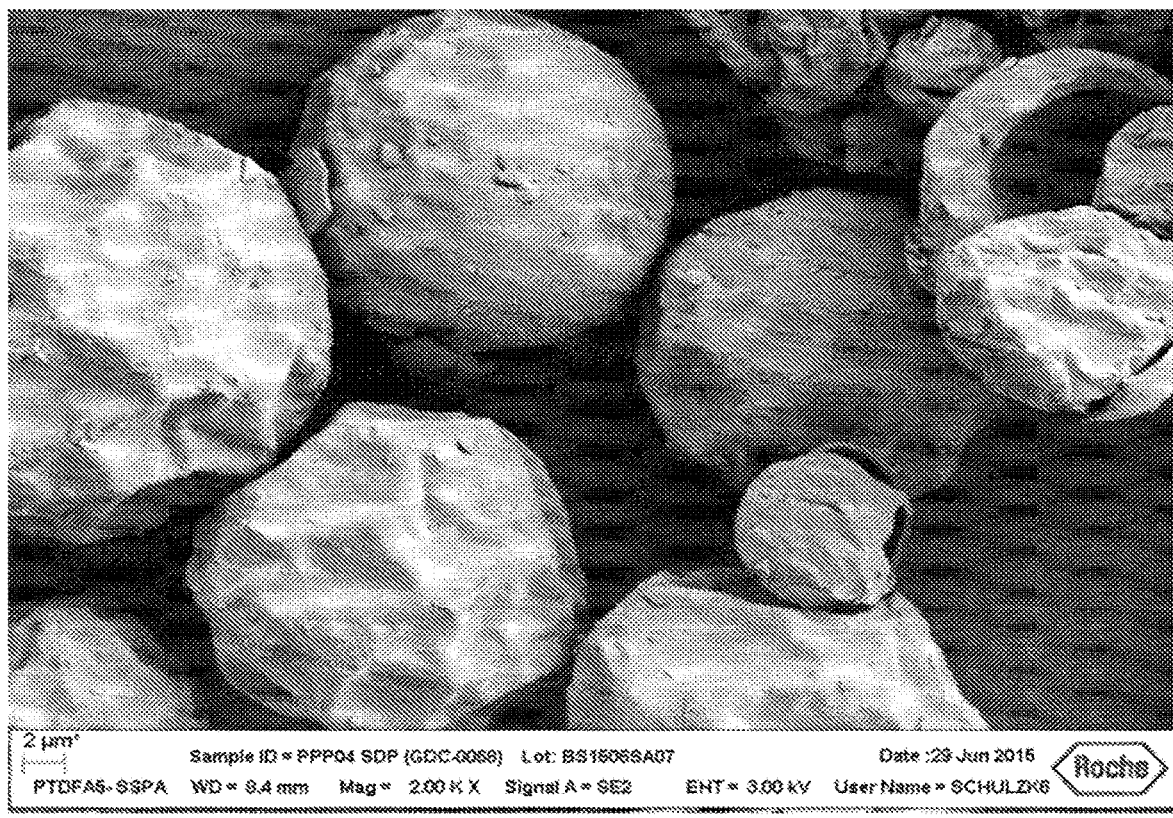
FIG. 10 illustrates a SEM micrograph of spray dried material with rotary wheel nozzle i.e. of the material of batch BS1506SA07 of Example 13 (Table 20) obtained using a Zeiss Sigma VP (Carl Zeiss Microscopy GmbH, Oberkochen/DE). Spherical particles of nearly uniform size are visible.

Example 7—General Procedure for the Conversion of Ipatasertib Monohydrochloride Ethyl Acetate Solvate into Amorphous Ipatasertib Monohydrochloride Using Rotary Wheel Type Spray-Dryer Dried ipatasertib monohydrochloride ethyl acetate solvate (typically comprising 2-8% wt EtOAc) was dissolved at 15 to 30° C. in purified water. The obtained solution containing 10 to 30% by wt. of solids was subsequently fed to the spray-dryer unit (Niro Production Minor™ Spray Dryer from GEA Process Engineering, Soeborg, DK) and was atomized in the drying chamber using the appropriate rotary wheel-type atomizing conditions or alternatively the appropriate two-fluid nozzle atomizing conditions. The fine mist created by the atomizer was mixed with a hot nitrogen stream as drying gas initiating evaporation of the water from the droplets. The feed rate of the solution was adjusted to achieve the desired gas outlet temperature. The drying gas carried the fine powder through the drying chamber out to the cyclone. The cyclone separated the powder from the drying gas and the powder was collected by gravity into drums. The substantially powder-free gas flowed into a filter bag housing where very fine particles were retained in the bag filters. The powder free gas was cooled down in a condenser where water condensation occurred and the drying gas after re-heating was re-circulated to the drying chamber (Flow Diagram of FIG. 8).

Example 8—Preparation of Amorphous Ipatasertib Monohydrochloride

Five batches of amorphous ipatasertib•HCl (130710450, 130710451, 130710452, 130810453, 130810454) were prepared according to the General Procedure of Example 7 with the exception that batch 130810454 was prepared with a two fluid nozzle spray-dryer instead of a rotary wheel type spray-dryer. Amounts of reactants employed, process parameters and analytical results are depicted in Table 13. All five batches were obtained within 1 to 2 hours. The four batches using a rotary wheel atomizing mode (batches no. 130710450, 130710451, 130710452, and 130810454) showed improved processability in subsequent drug product manufacturing.

TABLE 13

Process parameters and quality attributes of amorphous ipatasertib monohydrochloride.

| | | Batch | | | | |
|---|---|---|---|---|---|---|
| | | 130710450 | 130710451 | 130710452 | 130810453 | 130810454 |
| Amount of ipatasertib•HCl•EtOAc solvate | kg | 3.32 | 2.3 | 2.3 | 2.3 | 6.5 |
| Amount of water | kg | 9.0 | 9.2 | 9.2 | 9.2 | 19.5 |
| Ethyl acetate in ipatasertib | % | 7.2 | 7.2 | 7.2 | 7.2 | 7.2 |
| Concentration of solution | % m/m | 25 | 20 | 20 | 20 | 23.2 |
| Conditions | | | | | | |
| Atomizer wheel rotation | rpm | 15000 | 10400 | 28000 | | 15000 |
| Two-fluid nozzle gas | | | | | $N_2$ 13.9 kg/h/ 2.4 bar | |
| Feed solution rate | kg/h | 11.5-14.0 | 11.1-13.0 | 12.2-13.6 | 8.4-9.4 | 13.9-14.2 |
| Gas rate | kg/h | 450 | 450 | 450 | 450 | 450 |
| Gas inlet temperature | °C. | 160 | 170 | 170 | 180 | 160 |
| Gas outlet temperature | °C. | 90 | 100 | 100 | 120 | 90 |
| Condenser Temperature | °C. | 8-9 | 8 | 8 | 7.4-8 | 6-7 |
| Analytics | | | | | | |
| Ethyl acetate | % m/m | 0.37 | 0.28 | 0.19 | 0.34 | 0.33 |
| Water | % m/m | 2.3 | 2.2 | 3.1 | 2.1 | 2.6 |
| Purity (280 nm) | % area | 99.9 | 99.9 | 99.9 | 99.9 | 99.9 |
| Bulk density | gcm$^{-3}$ | 0.42 | 0.48 | 0.32 | 0.30 | 0.47 |
| Tapped density | gcm$^{-3}$ | 0.60 | 0.61 | 0.47 | 0.45 | 0.61 |
| Particle size [μm]: | $d_{10}$ | 14 | 17 | 8.4 | 6.6 | 12 |
| | $d_{50}$ | 40 | 45 | 21 | 20 | 36 |
| | $d_{90}$ | 79 | 88 | 42 | 58 | 72 |
| Solid state | X-Ray | Amorphous* | Amorphous* | Amorphous* | Amorphous* | Amorphous* |
| Yield (as/is) | % | 78.3 | 82.4 | 71 | 30.70 | 83.9 |
| Mass of spray dried Ipatasertib•HCl | kg | 2.60 | 1.895 | 1.636 | 0.705 | 5.456 |

*indicates absence of crystalline API.

Example 9—Preparation of Amorphous Ipatasertib Monohydrochloride

Five additional batches of amorphous ipatasertib monohydrochloride (140110401, 140110402, 140110403, 140110404, 140110405) were prepared according to the General Procedure of Example 7. Amounts of reactants employed, process parameters and analytical results are depicted in Table 14.

TABLE 14

Process parameters and quality attributes of amorphous ipatasertib monohydrochloride.

| | | Batch | | | | |
|---|---|---|---|---|---|---|
| | | 140110401 | 140110402 | 140110403 | 140110404 | 140110405 |
| Amount of ipatasertib•HCl•EtOAc solvate | kg | 4.0 | | 2.0 | | 4.0 |
| Amount of water | kg | 33.44 | | 7.36 | | 8.48 |
| Ethylacetate in ipatasertib | % | 6.4 | | 6.4 | | 6.4 |
| Concentration of solution | % m/m | 10 | | 20 | | 30 |
| Conditions | | | | | | |
| Atomizer wheel rotation | rpm | 15080 | 28110 | 21600 | 15080 | 28110 |
| Feed solution rate | kg/h | 8.5-9.5 | 11.6-13.3 | 9.4-11.2 | 12.0-13.2 | 8.6-11.4 |
| Drying gas rate | kg/h | 350 | 450 | 400 | 450 | 350 |

TABLE 14-continued

Process parameters and quality attributes of amorphous ipatasertib monohydrochloride.

|  |  | Batch | | | | |
| --- | --- | --- | --- | --- | --- | --- |
|  |  | 140110401 | 140110402 | 140110403 | 140110404 | 140110405 |
| Gas inlet temperature | °C. | 150 | 150 | 175 | 150 | 150 |
| Gas outlet temperature | °C. | 80 | 80 | 105 | 80 | 80 |
| Condenser temperature | °C. | 5-6 | 7-8 | 6.8-7.4 | 7-8 | 6-7 |
| Analytics |  |  |  |  |  |  |
| Ethyl acetate | % m/m | 0.09 | 0.08 | 0.13 | 0.27 | 0.35 |
| Water | % m/m | 3.5 | 3.5 | 2.5 | 4.0 | 2.9 |
| Purity (280 nm) | % area | 100.0 | 100.0 | 100.0 | 100.0 | 100.0 |
| Bulk density | gcm$^{-3}$ | 0.47 | 0.45 | 0.37 | 0.49 | 0.28 |
| Tapped density | gcm$^{-3}$ | 0.61 | 0.60 | 0.52 | 0.63 | 0.40 |
| Particle size [μm]: | $d_{10}$ | 11.4 | 7 | 9.4 | 12.5 | 9.3 |
|  | $d_{50}$ | 31 | 20 | 27 | 47 | 26 |
|  | $d_{90}$ | 64 | 46 | 61 | 108 | 57 |
| Solid state | X-Ray | amorphous* | amorphous* | amorphous* | amorphous* | amorphous* |
| Yield (as/is) | % | 74 |  | 73 |  | 78 |

*indicates absence of crystalline API.

Example 10—Preparation of Amorphous Ipatasertib Monohydrochloride

Five additional batches of amorphous ipatasertib monohydrochloride (140110406, 140110407, 140110408, 140110409, 140110410) were prepared according to the General Procedure of Example 7. Amounts of reactants employed, process parameters and analytical results are depicted in Table 15.

TABLE 15

Process parameters and quality attributes of amorphous ipatasertib monohydrochloride.

|  |  | Batch | | | | |
| --- | --- | --- | --- | --- | --- | --- |
|  |  | 140110406 | 140110407 | 140110408 | 140110409 | 140110410 |
| Amount of ipatasertib•HCl•EtOAc solvate | kg | 4.0 |  | 2.0 |  | 4.0 |
| Amount of water | kg | 33.44 |  | 7.36 |  | 8.48 |
| Ethylacetate in ipatasertib | % | 6.4 |  | 6.4 |  | 6.4 |
| Concentration of Solution | % m/m | 10 |  | 20 |  | 30 |
| Conditions |  |  |  |  |  |  |
| Atomizer wheel rotation | rpm | 15000 | 28110 | 21600 | 15080 | 28110 |
| Feed solution rate | kg/h | 10.2-10.8 | 6.7-7.5 | 9.4-10.4 | 6.5-8.0 | 9.4-12.2 |
| Drying gas rate | kg/h | 450 | 350 | 400 | 350 | 450 |
| Gas inlet temperature | °C. | 200 | 200 | 175 | 200 | 200 |
| Gas outlet temperature | °C. | 130 | 130 | 105 | 130 | 130 |
| Condenser temperature | °C. | 7-8 | 6-7 | 6-7 | 6-7 | 6-7 |
| Analytics |  |  |  |  |  |  |
| Ethyl acetate | % m/m | 0.08 | 0.06 | 0.13 | 0.26 | 0.28 |
| Water | % m/m | 4.8 | 4.2 | 3.4 | 3.7 | 1.6 |
| Purity (280 nm) | % area | 99.9 | 99.9 | 99.9 | 99.9 | 99.9 |
| Bulk density | gcm$^{-3}$ | 0.41 | 0.29 | 0.34 | 0.27 | 0.18 |
| Tapped density | gcm$^{-3}$ | 0.54 | 0.43 | 0.50 | 0.39 | 0.30 |

TABLE 15-continued

Process parameters and quality attributes of amorphous ipatasertib monohydrochloride.

| | | Batch | | | | |
|---|---|---|---|---|---|---|
| | | 140110406 | 140110407 | 140110408 | 140110409 | 140110410 |
| Particle size [µm]: | $d_{10}$ | 10.2 | 7.1 | 9.3 | 11.3 | 8.1 |
| | $d_{50}$ | 26 | 16 | 26 | 35 | 23 |
| | $d_{90}$ | 53 | 28 | 58 | 79 | 50 |
| Polymorphy | X-Ray | amorphous* | amorphous* | amorphous* | amorphous* | amorphous* |
| Yield (as/is) | % | | 64 | 51 | 72 | |

*indicates absence of crystalline API.

Example 11—Preparation of Amorphous Ipatasertib Monohydrochloride

One additional batch of amorphous ipatasertib monohydrochloride (140110411) was prepared according to the General Procedure of Example 7. Amounts of reactants employed, process parameters and analytical results are depicted in Table 16.

TABLE 16

Process parameters and quality attributes of amorphous ipatasertib monohydrochloride.

| | | Batch 140110411 |
|---|---|---|
| Amount of ipatasertib•HCl•EtOAc solvate | kg | 2.0 |
| Amount of water | kg | 7.36 |
| Ethylacetate in ipatasertib | % | 6.4 |
| Concentration of solution | % m/m | 20 |
| Conditions | | |
| Atomizer wheel rotation | rpm | 15000 |
| Feed solution rate | kg/h | 9.2-10.4 |
| Drying gas rate | kg/h | 450 |
| Gas inlet temperature | °C. | 160 |

TABLE 16-continued

Process parameters and quality attributes of amorphous ipatasertib monohydrochloride.

| | | Batch 140110411 |
|---|---|---|
| Gas outlet temperature | °C. | 90 |
| Condenser temperature | °C. | 6-7 |
| Analytics | | |
| Ethyl acetate | % m/m | 0.16 |
| Water | % m/m | 2.9 |
| Purity (280 nm) | % area | 99.9 |
| Bulk density | gcm$^{-3}$ | 0.37 |
| Tapped density | gcm$^{-3}$ | 0.51 |
| Particle size [µm]: | $d_{10}$ | 9.2 |
| | $d_{50}$ | 27 |
| | $d_{90}$ | 58 |
| Polymorphy | X-Ray | amorphous* |
| Yield (as/is) | % | 51 |

*indicates absence of crystalline API.

Example 12—Preparation of Amorphous Ipatasertib Monohydrochloride

Three additional batches of amorphous ipatasertib monohydrochloride (140210412, 140210413, 140210414) were prepared according to the General Procedure of Example 7. Amounts of reactants employed, process parameters and analytical results are depicted in Table 17.

TABLE 17

Process parameters and quality attributes of amorphous ipatasertib monohydrochloride.

| | | Batch | | |
|---|---|---|---|---|
| | | 140210412 | 140210413 | 140210414 |
| Amount of ipatasertib•HCl•EtOAc solvate | kg | 5.4 | 9.5 | 9.5 |
| Amount of water | kg | 14.88 | 79.80 | 24.35 |
| Ethyl acetate in ipatasertib | % | 6.11 | 6.0 | 6.0 |
| Concentration of solution | % m/m | 25 | 10 | 26 |
| Conditions | | | | |
| Atomizer wheel rotation | rpm | 15080 | 16570 | 11060 |
| Feed solution rate | kg/h | 14.0-14.3 | 9.8-10.5 | 11.5-12.5 |
| Drying gas rate | kg/h | 450 | 400 | 400 |
| Gas inlet temperature | °C. | 160 | 170 | 165 |
| Gas outlet temperature | °C. | 90 | 100 | 95 |

TABLE 17-continued

Process parameters and quality attributes of amorphous ipatasertib monohydrochloride.

| | | Batch | | |
|---|---|---|---|---|
| | | 140210412 | 140210413 | 140210414 |
| Condenser temperature | ° C. | 7-8 | 6-7 | 6-7 |
| Analytics | | | | |
| Ethyl acetate | % m/m | 0.39 | 0.10 | 0.44 |
| Water | % m/m | 2.7 | 3.7 | 2.3 |
| Purity (280 nm) | % area | 100.0 | 100.0 | 100.0 |
| Bulk density | gcm$^{-3}$ | 0.47 | 0.45 | 0.48 |
| Tapped density | gcm$^{-3}$ | 0.60 | 0.59 | 0.57 |
| Particle size [µm]: | $d_{10}$ | 13 | 10 | 18 |
| | $d_{50}$ | 46 | 28 | 53 |
| | $d_{90}$ | 94 | 56 | 109 |
| Polymorphy | X-Ray | amorphous* | amorphous* | amorphous* |
| Yield (as/is) | % | 83 | 86 | 86 |

*indicates absence of crystalline API.

Example 13—Preparation of Amorphous Ipatasertib Monohydrochloride

Twenty additional batches of amorphous ipatasertib monohydrochloride (140910415-141210426 and BS1506SA01-BS1506SA08) were prepared according to the General Procedure of Example 7. Amounts of reactants employed, process parameters and analytical results are depicted in Tables 18, 19 and 20.

The process conditions as employed e.g. in Table 20 enabled excellent yields of 90 to 94% "as/is" and of 96 to 100%: "corrected".

TABLE 18

Process parameters and quality attributes of amorphous ipatasertib monohydrochloride.

| | | Batch | | |
|---|---|---|---|---|
| | | 140910415 | 140910416 | 140910417 |
| Amount of ipatasertib•HCl•EtOAc solvate | kg | 8.00 | 10.00 | 10.00 |
| Amount of water | kg | 29.05 | 36.3 | 36.2 |
| Water in ipatasertib | % | 0.7 | 0.7 | 0.7 |
| Ethylacetate in ipatasertib | % | 7.4 | 7.4 | 7.4 |
| Concentration of Solution | % m/m | 20 | 20 | 20 |
| Conditions | | | | |
| Atomizer wheel rotation | rpm | 22090 | 22090 | 22090 |
| Feed solution rate | kg/h | 10.4-12.1 | 11.3-12.2 | 11.2-11.9 |
| Drying gas rate | kg/h | 400 | 400 | 400 |
| Gas inlet temperature | ° C. | 175 | 175 | 175 |
| Gas outlet temperature | ° C. | 105 | 105 | 105 |
| Condenser temperature | ° C. | 7-8 | 7-8 | 7-8 |
| Analytics | | | | |
| Ethylacetate | % m/m | 0.25 | 0.23 | 0.23 |
| Water | % m/m | 2.4 | (4.7) | 2.8 |
| Bulk density | gcm$^{-3}$ | 0.42 | 0.40 | 0.39 |
| Tapped density | gcm$^{-3}$ | 0.57 | 0.55 | 0.55 |
| Particle size [µm]: | $d_{10}$ | 11 | 10 | 11 |
| | $d_{50}$ | 29 | 27 | 27 |
| | $d_{90}$ | 56 | 52 | 54 |
| Polymorphy | X-Ray | amorph.* | amorph.* | amorph.* |
| Yield "as/is" | % | 85.9 | 88.7 | 91.2 |
| Yield "corrected" | % | (92.5) | (95.6) | (98.2) |
| Mass of spray dried ipatasertib•HCl | kg | 6.87 | 8.87 | 9.115 |
| Purity | % area | 99.9 | 99.9 | 99.9 |

TABLE 18-continued

Process parameters and quality attributes of amorphous ipatasertib monohydrochloride.

| | | Batch | | |
|---|---|---|---|---|
| | | 140910418 | 140910419 | 140910420 |
| Amount of ipatasertib•HCl•EtOAc solvate | kg | 8.00 | 12.0 | 12.0 |
| Amount of water | kg | 29.05 | 29.9 | 46.4 |
| Water in ipatasertib | % | 0.7 | 0.7-1.2 | 1.2 |
| Ethylacetate in ipatasertib | % | 7.4 | 7.4-2.6 | 2.6 |
| Concentration of Solution | % m/m | 20 | 27.5 | 20 |
| Conditions | | | | |
| Atomizer wheel rotation | rpm | 22090 | 16500 | 28000 |
| Feed solution rate | kg/h | 11.5-11.9 | 13.5 14.7 | 11.8-12.2 |
| Drying gas rate | kg/h | 400 | 450 | 400 |
| Gas inlet temperature | °C. | 175 | 175 | 175 |
| Gas outlet temperature | °C. | 105 | 105 | 105 |
| Condenser temperature | °C. | 7-8 | 8-9 | 7-8 |
| Analytics | | | | |
| Ethylacetate | % m/m | 0.25 | 0.20 | 0.04 |
| Water | % m/m | 2.6 | 2.5 | 3.1 |
| Bulk density | gcm$^{-3}$ | 0.39 | 0.44 | 0.32 |
| Tapped density | gcm$^{-3}$ | 0.55 | 0.58 | 0.44 |
| Particle size [μm]: | $d_{10}$ | 10 | 11 | 9.7 |
| | $d_{50}$ | 26 | 33 | 24 |
| | $d_{90}$ | 52 | 67 | 47 |
| Polymorphy | X-Ray | amorph.* | amorph.* | amorph.* |
| Yield "as/is" | % | 91.8 | 96.9 | 95 |
| Yield "corrected" | % | (98.8) | (99.4) | (94.5) |
| Mass of spray dried ipatasertib•HCl | kg | 7.34 | 11.63 | 11.40 |
| Purity | % area | 99.9 | 100.0 | 99.9 |

*indicates absence of crystalline API.

TABLE 19

Process parameters and quality attributes of amorphous ipatasertib monohydrochloride.

| | | Batch | | |
|---|---|---|---|---|
| | | 141210421 | 141210422 | 141210423 |
| Amount of ipatasertib•HCl•EtOAc solvate | kg | 12.0 | 12.0 | 12.40 |
| Amount of water | kg | 46.4 | 43.5 | 46.8 |
| Water in ipatasertib | % | 1.2 | 0.9 | 1.2/0.9 |
| Ethylacetate in ipatasertib | % | 2.6 | 7.5 | 2.6-7.5 |
| Concentration of Solution | % m/m | 20 | 20 | 20 |
| Conditions | | | | |
| Atomizer wheel rotation | rpm | 22000 | 22000 | 22000 |
| Feed solution rate | kg/h | 11.2-11.4 | 11.0-11.6 | 11.1-11.5 |
| Drying gas rate | kg/h | 400 | 400 | 400 |
| Gas inlet temperature | °C. | 175 | 175 | 175 |
| Gas outlet temperature | °C. | 105 | 105 | 105 |
| Condenser temperature | °C. | 7-8 | 7-8 | 7-8 |
| Analytics | | | | |
| Ethylacetate | % m/m | 0.04 | 0.27 | 0.10 |
| Water | % m/m | 3.0 | 2.8 | 2.4 |
| Bulk density | gcm$^{-3}$ | 0.38 | 0.37 | 0.39 |
| Tapped density | gcm$^{-3}$ | 0.55 | 0.54 | 0.55 |
| Particle size [μm]: | $d_{10}$ | 10 | 9.6 | 10 |
| | $d_{50}$ | 28 | 27 | 28 |
| | $d_{90}$ | 56 | 54 | 56 |

TABLE 19-continued

Process parameters and quality attributes of amorphous ipatasertib monohydrochloride.

| | | | | |
|---|---|---|---|---|
| Polymorphy | X-Ray | amorph.* | amorph.* | amorph.* |
| Yield "as/is" | % | 95.1 | 91.5 | 100 |
| Mass of spray dried ipatasertib•HCl | kg | 11.415 | 10.856 | 12.05 |
| Purity | % area | 99.7 | 99.8 | 99.8 |

| | | Batch | | |
|---|---|---|---|---|
| | | 141210424 | 141210425 | 141210426 |
| Amount of ipatasertib•HCl•EtOAc solvate | kg | 13.5 | 15.0 | 15.27 |
| Amount of water | kg | 49.0 | 35.5 | 55.8 |
| Water in ipatasertib | % | 0.9 | 0.9 | |
| Ethylacetate in ipatasertib | % | 7.5 | 7.5 | 7.5-6.8 |
| Concentration of Solution | % m/m | 20 | 27.5 | 20 |
| Conditions | | | | |
| Atomizer wheel rotation | rpm | 22000 | 16500 | 29290 |
| Feed solution rate | kg/h | 11.1-11.7 | 13.6-14.9 | 11.05-12.0 |
| Drying gas rate | kg/h | 400 | 450 | 400 |
| Gas inlet temperature | ° C. | 175 | 175 | 175 |
| Gas outlet temperature | ° C. | 105 | 105 | 105 |
| Condenser temperature | ° C. | 7-8 | 8-9 | 7-8 |
| Analytics | | | | |
| Ethylacetate | % m/m | 0.28 | 0.73 | 0.28 |
| Water | % m/m | 2.9 | 2.1 | 2.6 |
| Bulk density | gcm$^{-3}$ | 0.37 | 0.39 | 0.24 |
| Tapped density | gcm$^{-3}$ | 0.54 | 0.54 | 0.37 |
| Particle size [μm]: | $d_{10}$ | 9.5 | 11 | 8.5 |
| | $d_{50}$ | 27 | 39 | 21 |
| | $d_{90}$ | 54 | 80 | 43 |
| Polymorphy | X-Ray | amorph.* | amorph.* | amorph.* |
| Yield "as/is" | % | 92.2 | 91.7 | 91.22 |
| Mass of spray dried ipatasertib•HCl | kg | 12.45 | 13.61 | 13.75 |
| Purity | % area | 99.8 | 99.8 | 99.8 |

*indicates absence of crystalline API.

TABLE 20

Process parameters and quality attributes of amorphous ipatasertib monohydrochloride.

| | | Batch | | | |
|---|---|---|---|---|---|
| | | BS1506SA01 | BS1506SA02 | BS1506SA03 | BS1506SA04 |
| Amount of ipatasertib•HCl•EtOAc solvate | kg | 29.93 | 30.00 | 30.00 | 29.90 |
| Amount of water | kg | 110.0 | 110.0 | 110.0 | 110.0 |
| Water in ipatasertib | % | | | | |
| Ethylacetate in ipatasertib | % | 6.7 | 6.7 | 6.7 | 6.7-6.3 |
| Concentration of Solution | % m/m | 20 | 20 | 20 | 20 |
| Conditions | | | | | |
| Atomizer wheel rotation | rpm | 19060 | 19060 | 19060 | 19060 |
| Feed solution rate | kg/h | 10.4-11.1 | 10.3-11.3 | 9.8-11.4 | 10.7-11.3 |
| Drying gas rate | kg/h | 400 | 400 | 400 | 400 |
| Gas inlet temperature | ° C. | 175 | 175 | 175 | 175 |
| Gas outlet temperature | ° C. | 105 | 105 | 105 | 105 |
| Condenser temperature | ° C. | 5-8 | 6-8 | 6-9 | 6-9 |
| Analytics | | | | | |
| Ethylacetate | % m/m | 0.21 | 0.21 | 0.22 | 0.19 |
| Water | % m/m | 2.0 | 2.0 | 1.9 | 2.5 |
| Bulk density | gcm$^{-3}$ | 0.41 | 0.40 | 0.39 | 0.40 |
| Tapped density | gcm$^{-3}$ | 0.57 | 0.52 | 0.55 | 0.56 |
| Particle size [μm]: | $d_{10}$ | 11 | 11 | 12 | 11 |
| | $d_{50}$ | 31 | 31 | 31 | 30 |
| | $d_{90}$ | 64 | 64 | 62 | 62 |

TABLE 20-continued

Process parameters and quality attributes of amorphous ipatasertib monohydrochloride.

| | | | | | |
|---|---|---|---|---|---|
| Polymorphy | X-Ray | amorphous* | amorphous* | amorphous* | amorphous* |
| Yield "as/is" | % | 89.6 | 92.83 | 92.7 | 92.26 |
| Yield "corrected" | % | (96) | (99.5) | (99.35) | (98.14) |
| Mass of spray dried ipatasertib•HCl | kg | 26.88 | 27.85 | 27.82 | 27.68 |
| Purity | % area | 99.9 | 99.9 | 99.9 | 99.8 |

| | | Batch | | | |
|---|---|---|---|---|---|
| | | BS1506SA05 | BS1506SA06 | BS1506SA07 | BS1506SA08 |
| Amount of ipatasertib•HCl•EtOAc solvate | kg | 29.90 | 30.0 | 29.90 | 24.30 |
| Amount of water | kg | 109.8 | 110 | 110 | 90.0 |
| Water in ipatasertib | % | | | | |
| Ethylacetate in ipatasertib | % | 6.3-6.6 | 6.6 | 6.6-6.4 | 6.4 |
| Concentration of Solution | % m/m | 20 | 20 | 20 | 20 |
| Conditions | | | | | |
| Atomizer wheel rotation | rpm | 19060 | 19060 | 19060 | 19060 |
| Feed solution rate | kg/h | 10.9-11.3 | 10.1-11.3 | 10.7-11.5 | 10.9-11.5 |
| Drying gas rate | kg/h | 400 | 400 | 400 | 400 |
| Gas inlet temperature | °C. | 175 | 175 | 175 | 175 |
| Gas outlet temperature | °C. | 105 | 105 | 105 | 105 |
| Condenser temperature | °C. | 6-9 | 6-9 | 7-9 | 7-9 |
| Analytics | | | | | |
| Ethylacetate | % m/m | 0.21 | 0.21 | 0.20 | 0.19 |
| Water | % m/m | 1.9 | 2.2 | 2.0 | 2.5 |
| Bulk density | gcm$^{-3}$ | 0.41 | 0.41 | 0.42 | 0.43 |
| Tapped density | gcm$^{-3}$ | 0.57 | 0.56 | 0.56 | 0.56 |
| Particle size [μm]: | $d_{10}$ | 13 | 12 | 13 | 13 |
| | $d_{50}$ | 33 | 32 | 32 | 34 |
| | $d_{90}$ | 65 | 63 | 65 | 68 |
| Polymorphy | X-Ray | amorphous* | amorphous* | amorphous* | amorphous* |
| Yield "as/is" | % | 92.1 | 93.07 | 93.6 | 93.8 |
| Yield "corrected" | % | (98.35) | (99.0) | (99.9) | (100.2) |
| Mass of spray dried ipatasertib•HCl | kg | 27.57 | 27.92 | 27.98 | 22.80 |
| Purity | % area | 99.9 | 99.9 | 99.9 | 99.8 |

*indicates absence of crystalline API.

Example 14—Characterization of Amorphous Ipatasertib Monohydrochloride

Various amorphous ipatasertib monohydrochloride batches prepared using rotary wheel-type spray-dryer as obtained in Table 18 and Table 20 of Example 13 were further characterized by shear cell testing similar to the characterization in Example 6 (Table 12) of amorphous ipatasertib monohydrochloride prepared using two-fluid nozzle spray-dryer.

Similar to the classification used by Jenike (Dietmar Schulze, Pulver and Schüttgüter, 2009 Springer Verlag Berlin/DE), one can define flow behaviour based on the flow function constant (ffc) as follows:

| | |
|---|---|
| ffc < 1 | not flowing |
| 1 < ffc < 2 | very cohesive |
| 2 < ffc < 4 | cohesive |
| 4 < ffc < 10 | easy-flowing |
| 10 < ffc | free-flowing |

The larger the flow function constant ffc, i.e., the smaller the ratio of the unconfined yield strength (σc) to the consolidation stress (σ1), the better a bulk solid's flow.

As is shown in the data of Table 21, amorphous ipatasertib monohydrochloride prepared using a rotary wheel-type spray-dryer exhibit substantially improved flow behavious (ffc up to 4.0) as compared to amorphous ipatasertib monohydrochloride prepared using a two-fluid nozzle spray-dryer of Example 6C' (Table 12, ffc 1.08).

TABLE 21

Shear cell testing of amorphous ipatasertib monohydrochloride of Table 18 and Table 20 of Example 13 as measured using an automated Ring Shear Tester RST-XS using a 30 mL shear cell (Dr. Dietmar Schulze Schüttgutmesstechnik, Wolfenbüttel, DE).

| Batch No | Pre-shear stress [PA] | Consolidation stress (σ1) [PA] | Flow Function Constant (ffc) |
|---|---|---|---|
| 140910415 | 1000 | 1710 | 3.3 |
| 140910416 | 1000 | 1731 | 2.8 |
| 140910417 | 1000 | 1726 | 2.9 |
| 140910418 | 1000 | 1730 | 3.1 |
| 140910419 | 1000 | 1729 | 3.5 |
| 140910420 | 1000 | 1733 | 2.4 |
| BS1506SA01 | 1000 | 1725 | 4.0 |
| BS1506SA02 | 1000 | 1701 | 3.5 |
| BS1506SA03 | 1000 | 1709 | 2.9 |
| BS1506SA04 | 1000 | 1707 | 3.2 |
| BS1506SA05 | 1000 | 1668 | 3.5 |
| BS1506SA06 | 1000 | 1683 | 3.2 |
| BS1506SA07 | 1000 | 1705 | 3.1 |
| BS1506SA08 | 1000 | 1686 | 3.4 |

What is claimed is:

1. A process for the manufacture of granules comprising an Akt inhibitor suitable for a pharmaceutical composition comprising the Akt inhibitor, a filler, a binder, and a moisture adsorbent, the process comprising the following steps:
   (b) preparing a pre-blend by mixing the filler and the moisture adsorbent with the AKT inhibitor followed by introduction of the pre-blend into a fluid-bed granulator;
   (c) preparing a granulation solution by dissolving the binder in a solvent followed by stirring until formation of a clear solution; and
   (d) spraying the granulation solution onto the pre-blend in the fluid-bed granulator to obtain wet granules.

2. A process for the manufacture of a pharmaceutical composition comprising an Akt inhibitor, a filler, a binder, a disintegrant, and a glidant, the process comprising the following steps:
   (b) preparing a pre-blend by mixing the filler and a moisture adsorbent with the AKT inhibitor followed by introduction of the pre-blend into a fluid-bed granulator;
   (c) preparing a granulation solution by dissolving the binder in a solvent followed by stirring until formation of a clear solution; and
   (d) spraying the granulation solution onto the pre-blend in the fluid-bed granulator to obtain wet granules;
   (e) drying the wet granules in the fluid-bed granulator; and
   (h) preparing a first blend by mixing a disintegrant and a glidant together with the dried granules from step (e) in a blender.

3. A process for the preparation of amorphous ipatasertib monohydrochloride suitable for a pharmaceutical composition comprising ipatasertib monohydrochloride and one or more pharmaceutically acceptable excipients selected from the group consisting of a filler, a binder, and a disintegrant, the process comprising the steps of:
   (a) dissolving a solvate of ipatasertib in a solvent, thereby forming a feed solution;
   (b) feeding the feed solution into a spray-dryer unit;
   (c) atomizing the feed solution in the drying chamber to yield a mist;
   (d) mixing the mist with a drying gas thereby evaporating the solvent and forming amorphous ipatasertib monohydrochloride powder;
   (e) separating the amorphous ipatasertib monohydrochloride powder from the drying gas; and
   (f) collecting the amorphous ipatasertib monohydrochloride powder.

4. The process of claim 3, further comprising the steps of:
   (g) directing the drying gas formed from a cyclone into a filter bag housing wherein very fine particles are retained in the bag filters;
   (h) cooling down the drying gas in a condenser to yield solvent condensation; and
   (i) re-heating and re-circulating the re-dried drying gas into the drying chamber.

5. The process according to claim 3, wherein the solvate of ipatasertib in step (a) comprises in the crystal lattice a solvent selected from the group consisting of methyl acetate, ethyl acetate, n-propyl acetate, isopropyl acetate, n-butyl acetate, isobutyl acetate, tert-butyl acetate, ethyl propanoate, methylethyl ketone, 2-pentanone, methylbutyl ketone, methylisobutyl ketone, diisopropyl ketone, diisobutyl ketone, and methyl-tert-butyl ether.

6. The process according to claim 3, wherein the solvate of ipatasertib in step (a) is ipatasertib monohydrochloride ethyl acetate solvate (ipatasertib•HCl•EtOAc).

7. The process according to claim 3, wherein the spray-dryer unit in step (b) is a rotary wheel type or a two-fluid nozzle atomizer.

8. The process according to claim 3, wherein the process is performed with process parameters as follows:
   feed solution of 20 to 25% (w/w) ipatasertib•HCl•EtOAc 75 to 80% (w/w) water;
   (ii) atomizer of a rotary wheel type atomizer or two-fluid nozzle;
   (iii) atomizer speed of 10000 to 28000 RPM in case of rotary wheel atomizer;
   (iv) atomizing gas pressure of 2.2 to 2.6 bar in case of two-fluid nozzle;
   (v) drying gas inlet temperature of 160 to 180° C.;
   (vi) drying gas outlet temperature of 90 to 120° C.;
   (vii) drying gas (nitrogen) of 450 kg/h, particularly in closed cycle mode; and
   (viii) condensing temperature (step (h)) of 5 to 9° C.

9. The process according to claim 1, further comprising step (a) prior to step (b):
   (a) sieving the filler and the moisture adsorbent by passing each through a mill.

10. The process according to claim 1, further comprising step (e) after step (d):
    (e) drying the wet granules from step (d) in the fluid-bed granulator.

11. The process according to claim 1, wherein the Akt inhibitor is (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one or a pharmaceutically acceptable salt thereof.

12. The process according to claim 1, wherein the Akt inhibitor is (S)-2-(4-chlorophenyl)-1-(4-((5R,7R)-7-hydroxy-5-methyl-6,7-dihydro-5H-cyclopenta[d]pyrimidin-4-yl)piperazin-1-yl)-3-(isopropylamino)propan-1-one (ipatasertib) or a pharmaceutically acceptable salt thereof in an amorphous form.

13. The process according to claim 1, wherein the pharmaceutical composition comprises 50 mg to 1000 mg of the Akt inhibitor.

14. The process according to claim 1, wherein the pharmaceutical composition comprises 20-40% wt of the Akt inhibitor.

15. The process according to claim 2, further comprising step (j):
    (j) preparing a second blend by mixing a lubricant with the first blend from step (h) in a blender.

16. The process according to claim 12, further comprising step (k):
    (k) compressing the second blend from claim 12 to form tablets using a tablet press and punches.

17. The process according to claim 13, further comprising step (1):
    (l) coating the tablets from step (k) in a pan coater.

18. The process according to claim 2, further comprising step (a) prior to step (b):
    (a) sieving the filler and the moisture adsorbent by passing each through a mill.

19. The process according to claim 2, further comprising step (f):
    (f) sieving the granules by passing the granules through a mill.

20. The process according to claim 2, further comprising step (g) prior to step (h):
 (g) sieving the disintegrant and the glidant by passing each through a mill.

* * * * *